United States Patent
Solomon et al.

(10) Patent No.: US 6,768,003 B1
(45) Date of Patent: Jul. 27, 2004

(54) NUCLEIC ACIDS THAT ENCODE TRANSCRIPTIONAL ADAPTOR PROTEINS

(75) Inventors: William B. Solomon, New York, NY (US); Shaji Abraham, Brooklyn, NY (US)

(73) Assignee: The Research Foundation of State University of New York, Albany, NY (US)

( * ) Notice: Subject to any disclaimer, the term of this patent is extended or adjusted under 35 U.S.C. 154(b) by 0 days.

(21) Appl. No.: 09/668,119

(22) Filed: Sep. 22, 2000

(51) Int. Cl.[7] .................. C07H 21/04; C07H 21/00; C12N 15/63; C12N 15/85; C12N 15/87

(52) U.S. Cl. .................. 536/23.5; 536/23.1; 536/24.31; 435/455; 435/320.1

(58) Field of Search .............................. 536/23.5, 23.1, 536/24.31; 435/455, 320.1

(56) References Cited

U.S. PATENT DOCUMENTS 5,741,645 A * 4/1998 Orr et al.

OTHER PUBLICATIONS

Margolis et al (1997) Hum Gen 100:114–122.*
Database GenEMBL, accessed Mar. 1, 2002. Dec. 18, 1997. Accession No. HSU 80745.*
Philibert et al (1998) European Journal of Human Genetics 6:89–94.*
Database GenEMBL, accessed May 1, 2002, Apr. 3, 1998. Accession No. AF021108.*
Hillier et al, Database EST, accessed Mar. 1, 2002, Nov, 12, 1997. Accession No. AA664125.*
Naar et al., "Composite Co–activator ARC Mediates Chromatin–directed Transcriptional Activation", NATURE, 398:828–832(1999).

* cited by examiner

*Primary Examiner*—James Ketter
*Assistant Examiner*—Konstantina Katcheves
(74) *Attorney, Agent, or Firm*—Rogalskyj & Weyand LLP

(57) ABSTRACT

The present invention is directed to isolated nucleic acid molecules encoding protein, wherein the protein has transcriptional activator activity. Expression vectors and host cells comprising the nucleic acid molecules are also provided, as well as methods for increasing or decreasing the expression of the transcriptional activator protein in host cells. The invention further provides methods of screening a substance for the ability of the substance to modify, transcriptional activator protein function, and a method for isolating other transcriptional activator protein molecules.

17 Claims, 8 Drawing Sheets

```
CCGCCGCGACTTGGGCCTGGCTCTGTGACTGAGGCGGCGGCGGTGGCGGCCAAGCGGGATACGGGCGGCGGGAGCTGGGGAACAGGCATG    90
GACGTTTCCGGGCAAGAGACCGACTGGCGGAGACCGCCTTCCGGCAGAAGCTGGTCAGTCAAATCGAGGATGCCATGAGGAAAGCTGGTG   180
                                                                        M  R  K  A  G
TGGCACACAGTAAATCCAGCAAGGATATGGAGAGCCATGTTTTCCTGAAGGCCAAGACCCGGGACGAATACCTTTCTCTCGTGGCCAGGC   270
 V  A  H  S  K  S  S  K  D  M  E  S  H  V  F  L  K  A  K  T  R  D  E  Y  L  S  L  V  A  R
TCATTATCCATTTTCGAGACATTCATAACAAGAAATCTCAAGCTTCCGTCAGTGATCCTATGAATGCACTCCAGAGCCTGACTGGCGGAC   360
 L  I  I  H  F  R  D  I  H  N  K  K  S  Q  A  S  V  S  D  P  M  N  A  L  Q  S  L  T  G  G
CTGCTGCGGGAGCCGCTGGAATTGGCATGCCTCCTCGGGGCCCGGGACAGTCTCTGGGCGGGATGGGTAGCTTTGGTGCCATGGGACAGC   450
 P  A  A  G  A  A  G  I  G  M  P  P  R  G  P  G  Q  S  L  G  G  M  G  S  F  G  A  M  G  Q
CAATGTCTCTCTCAGGGCAGCCGCCTCCTGGGACCTCGGGGATGGCCCCTCACAGCATGGCTGTCGTGTCTACGGCAACTCCACAGACCC   540
 P  M  S  L  G  Q  P  P  P  G  T  S  G  M  A  P  H  S  M  A  V  V  S  T  A  T  P  Q  T
AGCTGCAGCTCCAGCAGGTGGCGCTGCAGCAGCAGCAGCAACAGCAGCAGTTCCAGCAGCAGCAGCAGGCGGCGCTACAGCAGCAGCAGC   630
 Q  L  Q  L  Q  Q  V  A  L  Q  Q  Q  Q  Q  Q  Q  F  Q  Q  Q  Q  Q  A  A  L  Q  Q  Q  Q
AGCAGCAGCAACAGCAGCAGTTCCAGGCTCAGCAGAGTGCCATGCAGCAGCAGTTCCAAGCAGTAGTGCAGCAGCAGCAGCAGCTCCAGC   720
 Q  Q  Q  Q  Q  Q  F  Q  A  Q  Q  S  A  M  Q  Q  Q  F  Q  A  V  V  Q  Q  Q  Q  Q  L  Q
AGCAGCAGCAGCAGCAGCAGCATCTAATTAAATTGCATCATCAAAATCAGCAACAGATACAGCAGCAGCAACAGCAGCTGCAGCGAATAC   810
 Q  Q  Q  Q  Q  Q  H  L  I  K  L  H  H  Q  N  Q  Q  Q  I  Q  Q  Q  Q  Q  L  Q  R  I
CACAGCTGCAGCTCCAACAACAGCAACAGCAGCAGCAGCAGCAGCAGCAGCAGCAGCAGGCTTTGGAGGCCCAGCCACCAATTCAGC     900
 A  Q  L  Q  L  Q  Q  Q  Q  Q  Q  Q  Q  Q  Q  Q  Q  Q  A  L  E  A  Q  P  P  I  Q
AGCCACCGATGCAGCAGCCACAGCCTCCGCCCTCCCAGGCTCTGCCCCAGCAGCTGCAGCAGATGCATCACACACAGCACCACCAGCCGC   990
 Q  P  P  M  Q  Q  P  Q  P  P  P  S  Q  A  L  P  Q  Q  L  Q  Q  M  H  H  T  Q  H  H  Q  P
CACCACAGCCCCAGCAGCCTCCAGTTGCTCAGAACCAACCATCACAACTCCCGCCACAGTCGCAGACCCAGCCTTTGGTGTCACAGGCGC  1080
 P  P  Q  P  Q  Q  P  P  V  A  Q  N  Q  P  S  Q  L  P  P  Q  S  Q  T  Q  P  L  V  S  Q  A
AAGCTCTCCCTGGACAAATGTTGTATACCCAACCACCACTGAAATTTGTCCGAGCTCCGATGGTGGTGCAGCAGCCCCCAGTGCAGCCC   1170
 Q  A  L  P  G  Q  M  L  Y  T  Q  P  P  L  K  F  V  R  A  P  M  V  V  Q  Q  P  P  V  Q  P
AGGTGCAGCAGCAGCAGACAGCAGTACAGACAGCTCAGGCTGCCCAGATGGTGGCTCCCGGAGTCCAGGTCAGCCAGAGCAGCCTCCCCA  1260
 Q  V  Q  Q  Q  Q  T  A  V  Q  T  A  Q  A  A  Q  M  V  A  P  G  V  Q  V  S  Q  S  S  L  P
TGCTGTCCTCGCCGTCACCGGGCCAGCAGGTGCAGACCCCGCAGTCGATGCCCCTCCCCCCAGCCGTCCCCGCAGCCCGGCCAGCCCA   1350
 M  L  S  S  P  S  P  G  Q  Q  V  Q  T  P  Q  S  M  P  P  P  P  Q  P  S  P  Q  P  G  Q  P
GCTCACAGCCCAACTCCAACGTCAGCTCTGGCCCTGCCCCATCTCCCAGTAGCTTCCTGCCCAGCCCCTCACCGCAGCCCTCCCAGAGCC  1440
 S  S  Q  P  N  S  N  V  S  S  G  P  A  P  S  P  S  S  F  L  P  S  P  S  P  Q  P  S  Q  S
CAGTGACGGCGCGGACCCCACAGAACTTCAGTGTCCCCTCACCTGGACCTTTAAACACACCTGTGAACCCCAGCTCTGTCATGAGCCCAG  1530
 P  V  T  A  R  T  P  Q  N  F  S  V  P  S  P  G  P  L  N  T  P  V  N  P  S  S  V  M  S  P
CTGGCTCCAGCCAGGCTGAGGAGCAGCAGTACCTGGACAAGCTGAAGCAGCTGTCGAAGTACATCGAGCCCCTGCGCCGCATGATCAACA  1620
 A  G  S  S  Q  A  E  E  Q  Q  Y  L  D  K  L  K  Q  L  S  K  Y  I  E  P  L  R  R  M  I  N
AGATCGACAAGAACGAAGACAGAAAAAAGGACCTGAGTAAGATGAAGAGCCTTCTGGACATTCTGACAGACCCCTCGAAGCGGTGTCCCC  1710
 K  I  D  K  N  E  D  R  K  K  D  L  S  K  M  K  S  L  L  D  I  L  T  D  P  S  K  R  C  P
```

Fig. 4

SEQUENCE LISTING

<160> NUMBER OF SEQ ID NOS: 8

<210> SEQ ID NO 1
<211> LENGTH: 1740
<212> TYPE: DNA
<213> ORGANISM: Homo sapiens

<400> SEQUENCE: 1

```
atgaggaaag ctggtgtggc acacagtaaa tccagcaagg atatggagag ccatgttttc      60
ctgaaggcca agacccggga cgaatacctt tctctcgtgg ccaggctcat tatccatttt     120
cgagacattc ataacaagaa atctcaagct tccgtcagtg atcctatgaa tgcactccag     180
agcctgactg gcggacctgc tgcgggagcc gctggaattg gcatgcctcc tcggggcccg     240
ggacagtctc tgggcgggat gggtagcttt ggtgccatgg gacagccaat gtctctctca     300
gggcagccgc ctcctgggac ctcggggatg gccctcaca gcatggctgt cgtgtctacg     360
gcaactccac agacccagct gcagctccag caggtggcgc tgcagcagca gcagcaacag     420
cagcagttcc agcagcagca gcaggcggcg ctacagcagc agcagcagca gcagcaacag     480
cagcagttcc aggctcagca gagtgccatg cagcagcagt tccaagcagt agtgcagcag     540
cagcagcagc tccagcagca gcagcagcag cagcagcatc taattaaatt gcatcatcaa     600
aatcagcaac agatacagca gcagcaacag cagctgcagc gaatagcaca gctgcagctc     660
caacaacagc aacagcagca gcagcagcag cagcagcagc agcagcaggc tttggaggcc     720
cagccaccaa ttcagcagcc accgatgcag cagccacagc ctccgccctc ccaggctctg     780
ccccagcagc tgcagcagat gcatcacaca cagcaccacc agccgccacc acagccccag     840
cagcctccag ttgctcagaa ccaaccatca caactcccgc cacagtcgca gacccagcct     900
```

-continued

```
ttggtgtcac aggcgcaagc tctccctgga caaatgttgt atacccaacc accactgaaa      960
tttgtccgag ctccgatggt ggtgcagcag cccccagtgc agcccaggt gcagcagcag     1020 cagacagcag tacagacagc tcaggctgcc cagatggtgg ctcccggagt ccaggtcagc     1080
cagagcagcc tccccatgct gtcctcgccg tcaccgggcc agcaggtgca gaccccgcag     1140
tcgatgcccc ctcccccca gccgtccccg cagcccggcc agcccagctc acagcccaac     1200
tccaacgtca gctctggccc tgccccatct cccagtagct tcctgcccag cccctcaccg     1260
cagccctccc agagcccagt gacggcgcgg accccacaga acttcagtgt cccctcacct     1320 ggaccttaa acacacctgt gaaccccagc tctgtcatga gcccagctgg ctccagccag     1380
gctgaggagc agcagtacct ggacaagctg aagcagctgt cgaagtacat cgagcccctg     1440
cgccgcatga tcaacaagat cgacaagaac gaagacagaa aaaaggacct gagtaagatg     1500
aagagccttc tggacattct gacagacccc tcgaagcggt gtccctgaa gaccttgcaa     1560 aagtgtgaga tcgccctgga gaaactcaag aatgacatgc ggtgcccact ccccaccgc     1620 ccccggtgcc accgaccaaa cagcagtacc tatgccagcc gctcctggat gccgtcctgg     1680
ccaacatccg ctcacctgtc ttcaaccatt ccctgtaccg cacattcgtt ccagccatga     1740
```

<210> SEQ ID NO 2
<211> LENGTH: 3334
<212> TYPE: DNA
<213> ORGANISM: Homo sapiens

<400> SEQUENCE: 2

```
ccggcgcgac ttgggcctgg ctctgtgact gaggcggcgg cggtggcggc caagcgggat       60
acgggcggcg ggagctgggg aacaggcatg gacgtttccg ggcaagagac cgactggcgg      120
agaccgcctt ccggcagaag ctggtcagtc aaatcgagga tgccatgagg aaagctggtg      180
tggcacacag taaatccagc aaggatatgg agagccatgt tttcctgaag gccaagaccc      240
gggacgaata ccttctctc gtggccaggc tcattatcca ttttcgagac attcataaca      300
agaaatctca agcttccgtc agtgatccta tgaatgcact ccagagcctg actggcggac      360
ctgctgcggg agccgctgga attggcatgc ctcctcgggg cccgggacag tctctgggcg      420
ggatgggtag cttggtgcc atgggacagc caatgtctct ctcagggcag ccgcctcctg      480
ggacctcggg gatggcccct cacagcatgg ctgtcgtgtc tacggcaact ccacagaccc      540
agctgcagct ccagcaggtg gcgctgcagc agcagcagca acagcagcag ttccagcagc      600
agcagcaggc ggcgctacag cagcagcagc agcagcagca acagcagcag ttccaggctc      660
agcagagtgc catgcagcag cagttccaag cagtagtgca gcagcagcag cagctccagc      720
agcagcagca gcagcagcag catctaatta aattgcatca tcaaaatcag caacagatac      780
agcagcagca acagcagctg cagcgaatag cacagctgca gctccaacaa cagcaacagc      840
agcagcagca gcagcagcag cagcagcagc aggctttgga ggcccagcca ccaattcagc      900
agccaccgat gcagcagcca cagcctccgc cctcccaggc tctgccccag cagctgcagc      960
agatgcatca cacacagcac caccagccgc caccacagcc cagcagcct ccagttgctc     1020 agaaccaacc atcacaactc ccgccacagt cgcagaccca gcctttggtg tcacaggcgc     1080
aagctctccc tggacaaatg ttgtatacc aaccaccact gaaatttgtc cgagctccga     1140
tggtggtgca gcagcccca gtgcagcccc aggtgcagca gcagcagaca gcagtacaga     1200
cagctcaggt tgcccagatg gtggctcccg gagtccaggt cagccagagc agcctcccca     1260
tgctgtcctc gccgtcaccg ggccagcagg tgcagacccc gcagtcgatg cccccctccc     1320
```

```
cccagccgtc cccgcagccc ggccagccca gctcacagcc caactccaac gtcagctctg    1380
gccctgcccc atctcccagt agcttcctgc ccagcccctc accgcagccc tcccagagcc    1440
cagtgacggc gcggacccca cagaacttca gtgtcccctc acctggacct ttaaacacac    1500
ctgtgaaccc cagctctgtc atgagcccag ctggctccag ccaggctgag gagcagcagt    1560
acctggacaa gctgaagcag ctgtcgaagt acatcgagcc cctgcgccgc atgatcaaca    1620
agatcgacaa gaacgaagac agaaaaaagg acctgagtaa gatgaagagc cttctggaca    1680
ttctgacaga cccctcgaag cggtgtcccc tgaagacctt gcaaaagtgt gagatcgccc    1740
tggagaaact caagaatgac atgcggtgcc cactccccca ccgcccccgg tgccaccgac    1800
caaacagcag tacctatgcc agccgctcct ggatgccgtc ctggccaaca tccgctcacc    1860
tgtcttcaac cattccctgt accgcacatt cgttccagcc atgaccgcca ttcacggccc    1920
acccatcacg gccccagtgg tgtgcacccg gaagcgcagg cttgaggatg atgagcggca    1980
gagcatcccc agtgtgctcc agggtgaggt ggccaggctg accccaagt tcctggtaaa    2040 cctggaccct tctcactgca gcaacaatgg cactgtccac ctgatctgca agctggatga    2100
caaggacctc ccaagtgtgc caccactgga gctcagtgtg cccgctgact atcctgccca    2160
aagcccgctg tggatagacc ggcagtggca gtacgacgcc aacccctttc ctccagtcgg    2220
tgcaccgctg catgacctcc aggctgctgc agctcccgga caagcactcg gtcaccgcct    2280
tgctcaacac ctgggcccag agcgtccacc aggcctgcct ctcagccgcc tagccaagac    2340
tgcagggatg gcccgcagcc tcatcggggc caaggacaca cgcctcctgt cagacacttc    2400
taggtgttgg cttccttaga gagcctgggg ttaggttagc tttcctgctt ttatcttctg    2460
ccttggggac ctgccaaacg aaatcccaca cctgtacaga actgggatag cgcagtgga    2520 gcgggttgct tggggggcgt tggccgactt cttagagaag ccctccatg tgacttcctc    2580 ccaggagcca gatgcgatcc tcaggctgct ctcaccgtgg cctgtccacg gtccaggtcc    2640
atctcagcag cgtgagggtg cactcagggt gttgttagag cgtctcgtgt gtgctagacg    2700
cacccctact cgttcctata gaacacagag gacataggaa acccttaaaa cacacatggg    2760
attctctggt cacagttttg ggttcaggct atgctgcttt gggcaggtgg agcaccccc    2820 gaggaagcct gcaagtccag ggcacaggct gccttttgga ggggaggtct gcccataggt    2880
gctgctggct ccccgccacc agctgggcct cagccctcac ggcattcctg ctgagcaccg    2940
tgggcacccc agggagcagg ggcgtcaggg atcctgctgc cggcacccct gtgccgctgg    3000
catgagggcc gtgtccccac tgtgaaggat gaagagcaag gccctcagga cccgtgtcct    3060
cagagcacca cacactgagc acccagagac agcgggcttg gcagcgggcc gggccatgca    3120
gggagcgcct ccctatgttg cctgccactc tgggcaccgg ccagcaccct ctggtgagaa    3180
gaggtccccc cttttttatgt gcactacccc accatctgtg attataataa atttattatt    3240
cctgtggaaa aaaaaaaaa aaaaaaaaa aaaaaaaaa aaaaaaaaa aaaaaaaaa    3300 aaaaaaaaa aaaaaaaaa aaaaaaaaa aaaa    3334
```

<210> SEQ ID NO 3
<211> LENGTH: 579
<212> TYPE: PRT
<213> ORGANISM: Homo sapiens

<400> SEQUENCE: 3

```
Met Arg Lys Ala Gly Val Ala His Ser Lys Ser Ser Lys Asp Met Glu
 1               5                  10                  15
```

-continued

```
Ser His Val Phe Leu Lys Ala Lys Thr Arg Asp Glu Tyr Leu Ser Leu
             20                  25                  30

Val Ala Arg Leu Ile Ile His Phe Arg Asp Ile His Asn Lys Lys Ser
         35                  40                  45

Gln Ala Ser Val Ser Asp Pro Met Asn Ala Leu Gln Ser Leu Thr Gly
     50                  55                  60

Gly Pro Ala Ala Gly Ala Gly Ile Gly Met Pro Pro Arg Gly Pro
 65                  70                  75                  80

Gly Gln Ser Leu Gly Gly Met Gly Ser Phe Gly Ala Met Gly Gln Pro
                 85                  90                  95

Met Ser Leu Ser Gly Gln Pro Pro Gly Thr Ser Gly Met Ala Pro
                100                 105                 110

His Ser Met Ala Val Val Ser Thr Ala Thr Pro Gln Thr Gln Leu Gln
            115                 120                 125

Leu Gln Gln Val Ala Leu Gln Gln Gln Gln Gln Gln Gln Phe Gln
        130                 135                 140

Gln Gln Gln Gln Ala Ala Leu Gln Gln Gln Gln Gln Gln Gln Gln
145                 150                 155                 160

Gln Gln Phe Gln Ala Gln Ser Ala Met Gln Gln Phe Gln Ala
            165                 170                 175

Val Val Gln Gln Gln Gln Leu Gln Gln Gln Gln Gln Gln Gln
        180                 185                 190

His Leu Ile Lys Leu His His Gln Asn Gln Gln Ile Gln Gln Gln
        195                 200                 205

Gln Gln Gln Leu Gln Arg Ile Ala Gln Leu Gln Leu Gln Gln Gln Gln
    210                 215                 220

Gln Gln Gln Gln Gln Gln Gln Gln Gln Gln Gln Ala Leu Glu Ala
225                 230                 235                 240

Gln Pro Pro Ile Gln Gln Pro Met Gln Gln Pro Gln Pro Pro
            245                 250                 255

Ser Gln Ala Leu Pro Gln Gln Leu Gln Gln Met His His Thr Gln His
        260                 265                 270

His Gln Pro Pro Gln Pro Gln Gln Pro Val Ala Gln Asn Gln
    275                 280                 285

Pro Ser Gln Leu Pro Pro Gln Ser Gln Thr Gln Pro Leu Val Ser Gln
    290                 295                 300

Ala Gln Ala Leu Pro Gly Gln Met Leu Tyr Thr Gln Pro Pro Leu Lys
305                 310                 315                 320

Phe Val Arg Ala Pro Met Val Val Gln Gln Pro Pro Val Gln Pro Gln
            325                 330                 335

Val Gln Gln Gln Gln Thr Ala Val Gln Thr Ala Gln Ala Gln Met
        340                 345                 350

Val Ala Pro Gly Val Gln Val Ser Gln Ser Ser Leu Pro Met Leu Ser
    355                 360                 365

Ser Pro Ser Pro Gly Gln Gln Val Gln Thr Pro Gln Ser Met Pro Pro
    370                 375                 380

Pro Pro Gln Pro Ser Pro Gln Pro Gly Gln Pro Ser Ser Gln Pro Asn
385                 390                 395                 400

Ser Asn Val Ser Ser Gly Pro Ala Pro Ser Pro Ser Ser Phe Leu Pro
            405                 410                 415

Ser Pro Ser Pro Gln Pro Ser Gln Ser Pro Val Thr Ala Arg Thr Pro
            420                 425                 430
```

```
Gln Asn Phe Ser Val Pro Ser Pro Gly Pro Leu Asn Thr Pro Val Asn
        435                 440                 445

Pro Ser Ser Val Met Ser Pro Ala Gly Ser Ser Gln Ala Glu Glu Gln
    450                 455                 460

Gln Tyr Leu Asp Lys Leu Lys Gln Leu Ser Lys Tyr Ile Glu Pro Leu
465                 470                 475                 480

Arg Arg Met Ile Asn Lys Ile Asp Lys Asn Glu Asp Arg Lys Lys Asp
                485                 490                 495

Leu Ser Lys Met Lys Ser Leu Leu Asp Ile Leu Thr Asp Pro Ser Lys
            500                 505                 510

Arg Cys Pro Leu Lys Thr Leu Gln Lys Cys Glu Ile Ala Leu Glu Lys
            515                 520                 525

Leu Lys Asn Asp Met Arg Cys Pro Leu Pro His Arg Pro Arg Cys His
        530                 535                 540

Arg Pro Asn Ser Ser Thr Tyr Ala Ser Arg Ser Trp Met Pro Ser Trp
545                 550                 555                 560

Pro Thr Ser Ala His Leu Ser Ser Thr Ile Pro Cys Thr Ala His Ser
                565                 570                 575

Phe Gln Pro

<210> SEQ ID NO 4
<211> LENGTH: 15
<212> TYPE: PRT
<213> ORGANISM: Homo sapiens

<400> SEQUENCE: 4

Arg Arg Met Ile Asn Lys Ile Asp Lys Asn Glu Asp Arg Lys Lys
1               5                   10                  15

<210> SEQ ID NO 5
<211> LENGTH: 6
<212> TYPE: PRT
<213> ORGANISM: Homo sapiens

<400> SEQUENCE: 5

Gln Ser Ser Gln Ala Glu
1               5

<210> SEQ ID NO 6
<211> LENGTH: 107
<212> TYPE: PRT
<213> ORGANISM: Homo sapiens

<400> SEQUENCE: 6

Ala Leu Gln Gln Gln Gln Gln Gln Gln Phe Gln Gln Gln Gln
1               5                   10                  15

Ala Ala Leu Gln Gln Gln Gln Gln Gln Gln Gln Gln Gln Phe Gln
            20                  25                  30

Ala Gln Gln Ser Ala Met Gln Gln Phe Gln Ala Val Val Gln Gln
        35                  40                  45

Gln Gln Gln Leu Gln Gln Gln Gln Gln Gln His Leu Ile Lys
    50                  55                  60

Leu Arg Arg Gln Asn Gln Gln Ile Gln Gln Gln Gln Gln Leu
65                  70                  75                  80

Gln Arg Ile Ala Gln Leu Gln Leu Gln Gln Gln Gln Gln Gln
            85                  90                  95

Gln Gln Gln Gln Gln Gln Gln Gln Ala Leu Glu
            100                 105
```

```
<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: linker
      sequence

<400> SEQUENCE: 7
gaattcagat ctcccgggtc accgc                                           25

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: linker
      sequence

<400> SEQUENCE: 8
tgacccggga gatcgaattc                                                 20
```

NUCLEIC ACIDS THAT ENCODE TRANSCRIPTIONAL ADAPTOR PROTEINS

FIELD OF THE INVENTION

The present invention relates generally to a transcriptional adaptor protein, the gene encoding the protein and uses thereof.

BRIEF DESCRIPTION OF THE DRAWINGS

These and other features and advantages of this invention will be evident from the following detailed description of preferred embodiments when read in conjunction with the accompanying drawings in which:

FIG. 1A: Probes SA25, SA 21, SA11 were obtained as a partial cDNA fragments from the K562 TPA-Hemin subtracted cDNA library. SA25 hybridized to a novel 3.7 kb transcript TIG-1. SA21 hybridized to the TIMP-1 mRNA. SA11 hybridized to an EST of unknown function.

FIG. 2A: Representative northern blot using a partial cDNA fragment of TIG-1 as probe.

FIG. 3A: Representative Northern Blots of Tissues. Each lane contains 2 µg of poly A$^+$ mRNA.

The deduced open reading frame of the TIG-1 cDNA is shown (SEQ ID NO:1), as well as the amino acid sequence (SEQ ID NO:3) and the full nucleotide sequence (SEQ ID NO:2).

Underlined is the putative bipartite nuclear localization signal (SEQ ID NO:4: RRMINKIDKNEDRKK). The three circles underneath TAR represent a putative protein kinase C phosphorylation site. The sequence QSSQAE (SEQ ID NO:5) is a putative casein kinase II phosphorylation site. The filled in bars below the sequences NVSS and NFSV represent potential N-glycosylation sites.

Figure 5:
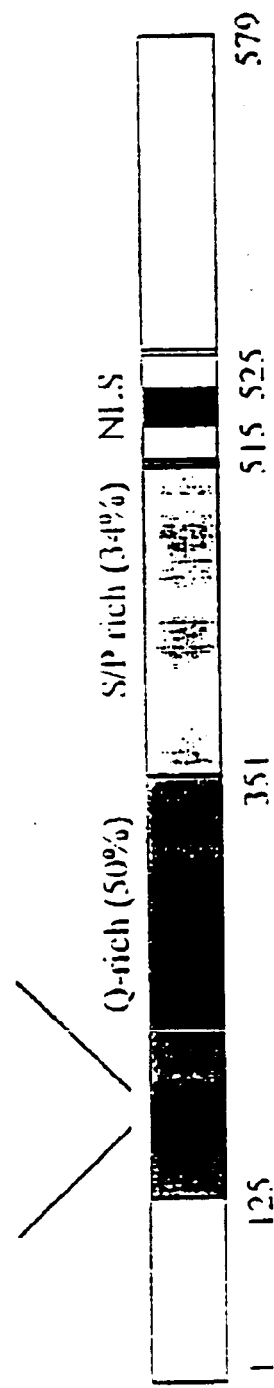

FIG. 5 shows a representation of the amino acid sequence of the TIG-1 protein: The glutamine and serine/proline rich domains are noted. The glutamine rich repeat sequences are shown (SEQ ID NO: 6). The putative nuclear localization signal is shown in black.

Figure 6B:
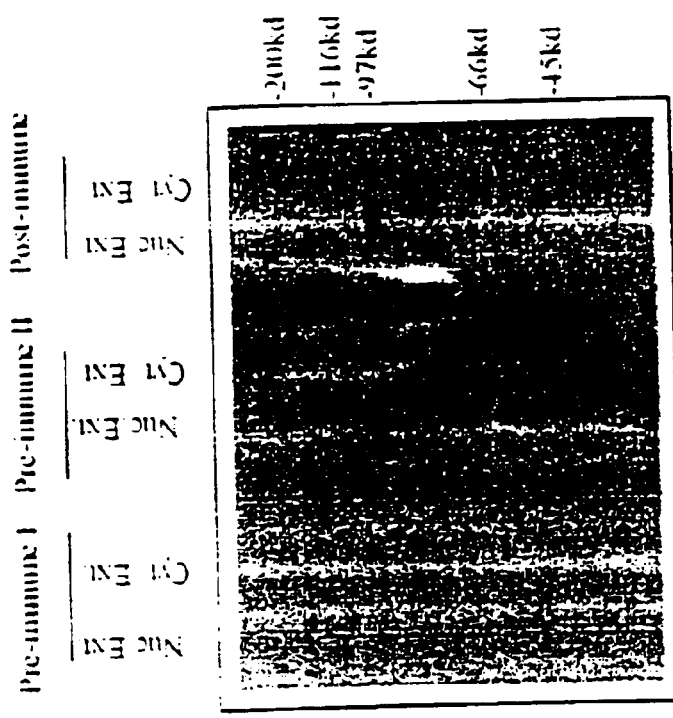
Figure 6A:
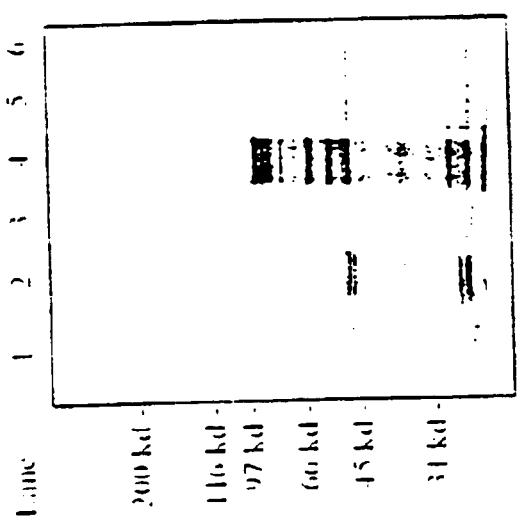

FIG. 6A shows a SDS-PAGE of in vitro translation products obtained from TIG-1 transcripts. Lane 4 contains translation products of TIG-1 sense transcripts. Lane 5 contains translation products of TIG-1 antisense transcripts. Lanes 2 and 3 contains translation products of NF-E2 sense and antisense transcripts respectively.

FIG. 6B shows a Western Blot analysis of K562 cytoplasmic and nuclear protein extracts. Each lane contains 50 µg of protein. Lanes 1 and 2 were blotted with preimmune serum which had been affinity purified with the carboxy terminal amino acids of TIG-1 protein. Lanes 3 and 4 were blotted with the supernatant fraction of the affinity purified preimmune serum. Lanes 5 and 6 were blotted with postimmune serum affinity purified with the carboxy terminal amino acids of TIG-1 protein.

FIGS. 7A–C are a Transient Transfection analysis of effect GAL4: TIG-1 fusion protein on CAT reporter gene expression. FIG. 7A shows a representation of the structure of the GAL4: TIG-1 fusion proteins and CAT gene reporter plasmid construct. FIG. 7B shows a representative CAT assay following 48 hours of transient expression of the GAL4: TIG-1 fusion proteins. FIG. 7C shows a bar graph showing mean and standard deviation of fold induction of CAT activity in each cell lysate. The fold induction is relative to the CAT activity of uninduced K562 cells. Differences in transfection efficiency were corrected for by cotransfection with pCMVβgal expression plasmid.

DETAILED DESCRIPTION OF THE INVENTION

Throughout this application various publications are referenced, many in parenthesis. Full citations for each of these publications are provided at the end of the Detailed Description and throughout the Detailed Description. The disclosures of each of these publications in their entireties are hereby incorporated by reference in this application.

The term "nucleic acid", as used herein, refers to either DNA or RNA. "Nucleic acid sequence" or "polynucleotide sequence" refers to a single- or double-stranded polymer of deoxyribonucleotide or ribonucleotide bases read from the 5' to the 3' end. It includes both self-replicating plasmids, infectious polymers of DNA or RNA, and nonfunctional DNA or RNA.

"Isolated" nucleic acid refers to nucleic acid which has been separated from an organism in a substantially purified form (i.e. substantially free of other substances originating from that organism), and to synthetic nucleic acid.

By a nucleic acid sequence "homologous to" or "complementary to", it is meant a nucleic acid that selectively hybridizes, duplexes or binds to DNA sequences encoding the protein or portions thereof when the DNA sequences encoding the protein are present in a genomic or cDNA library. A DNA sequence which is similar or complementary to a target sequence can include sequences which are shorter or longer than the target sequence so long as they meet the functional test set forth.

Typically, the hybridization is done in a Southern blot protocol using a 0.2×SSC, 0.1% SDS, 65° C. wash. The term "SSC" refers to a citrate-saline solution of 0.15M sodium chloride and 20 mM sodium citrate. Solutions are often expressed as multiples or fractions of this concentration. For example, 6×SSC refers to a solution having a sodium chloride and sodium citrate concentration of 6 times this amount or 0.9 M sodium chloride and 120 mM sodium citrate. 0.2×SSC refers to a solution 0.2 times the SSC concentration or 0.03M sodium chloride and 4 mM sodium citrate.

The phrase "nucleic acid molecule encoding" refers to a nucleic acid molecule which directs the expression of a specific protein or peptide. The nucleic acid sequences include both the DNA strand sequence that is transcribed into RNA and the RNA sequence that is translated into protein or peptide. The nucleic acid molecule includes both the full length nucleic acid sequences as well as non-full length sequences derived from the full length protein. It being further understood that the sequence includes the degenerate codons of the native sequence or sequences which may be introduced to provide codon preference in a specific host cell.

The term "located upstream" as used herein refers to linkage of a promoter upstream from a nucleic acid (DNA) sequence such that the promoter mediates transcription of the nucleic acid (DNA) sequence.

The term "vector", refers to viral expression systems, autonomous self-replicating circular DNA (plasmids), and includes both expression and nonexpression plasmids. Where a recombinant microorganism or cell is described as hosting an "expression vector," this includes both extrachromosomal circular DNA and DNA that has been incorporated into the host chromosome(s). Where a vector is being maintained by a host cell, the vector may either be stabley replicated by the cells during mitosis as an autonomous structure, or the vector may be incorporated within the host's genome.

The term "plasmid" refers to an autonomous circular DNA molecule capable of replication in a cell, and includes both the expression and nonexpression types. Where a recombinant microorganism or cell is described as hosting an "expression plasmid", this includes latent viral DNA integrated into the host chromosome(s). Where a plasmid is being maintained by a host cell, the plasmid is either being stabley replicated by the cell during mitosis as an autonomous structure, or the plasmid is incorporated within the host's genome.

The phrase "heterologous protein" or "recombinantly produced heterologous protein" refers to a peptide or protein of interest produced using cells that do not have an endogenous copy of DNA able to express the peptide or protein of interest. The cells produce the peptide or protein because they have been genetically altered by the introduction of the appropriate nucleic acid sequences. The recombinant peptide or protein will not be found in association with peptides or proteins and other subcellular components normally associated with the cells producing the peptide or protein.

The following terms are used to describe the sequence relationships between two or more nucleic acid molecules or polynucleotides, or between two or more amino acid sequences of peptides or proteins: "reference sequence", "comparison window", "sequence identity", "sequence homology", "percentage of sequence identity", "percentage of sequence homology", "substantial identity", and "substantial homology". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence.

Optimal alignment of sequences for aligning a comparison window may be conducted, for example, by the local homology algorithm of Smith and Waterman (1981), by the homology alignment algorithm of Needleman and Wunsch (1970), by the search for similarity method of Pearson and Lipman (1988), or by computerized implementations of these algorithms (GAP, BESTFIT, FASTA, and TFASTA in the Wisconsin Genetics Software Package Release 7.0, Genetics Computer Group, 575 Science Dr., Madison, Wis.).

As applied to nucleic acid molecules or polynucleotides, the terms "substantial identity" or "substantial sequence identity" mean that two nucleic acid sequences, when optimally aligned (see above), share at least 90 percent sequence identity, preferably at least 95 percent sequence identity, more preferably at least 96, 97, 98 or 99 percent sequence identity.

"Percentage nucleotide (or nucleic acid) identity" or "percentage nucleotide (or nucleic acid) sequence identity" refers to a comparison of the nucleotides of two nucleic acid molecules which, when optimally aligned, have approximately the designated percentage of the same nucleotides. For example, "95% nucleotide identity" refers to a comparison of the nucleotides of two nucleic acid molecules which when optimally aligned have 95% nucleotide identity. Preferably, nucleotide positions which are not identical differ by redundant nucleotide substitutions (the nucleotide substitution does not change the amino acid encoded by the particular codon).

As further applied to nucleic acid molecules or polynucleotides, the terms "substantial homology" or "substantial sequence homology" mean that two nucleic acid sequences, when optimally aligned (see above), share at least 90 percent sequence homology, preferably at least 95 percent sequence homology, more preferably at least 96, 97, 98 or 99 percent sequence homology.

"Percentage nucleotide (or nucleic acid) homology" or "percentage nucleotide (or nucleic acid) sequence homology" refers to a comparison of the nucleotides of two nucleic acid molecules which, when optimally aligned, have approximately the designated percentage of the same nucleotides or nucleotides which are not identical but differ by redundant nucleotide substitutions (the nucleotide substitution does not change the amino acid encoded by the particular codon). For example, "95% nucleotide homology" refers to a comparison of the nucleotides of two nucleic acid molecules which when optimally aligned have 95% nucleotide homology.

As applied to polypeptides, the terms "substantial identity" or "substantial sequence identity" mean that two peptide sequences, when optimally aligned, such as by the programs GAP or BESTFIT using default gap, share at least 90 percent sequence identity, preferably at least 95 percent sequence identity, more preferably at least 96, 97, 98 or 99 percent sequence identity.

"Percentage amino acid identity" or "percentage amino acid sequence identity" refers to a comparison of the amino acids of two polypeptides which, when optimally aligned, have approximately the designated percentage of the same amino acids. For example, "95% amino acid identity" refers to a comparison of the amino acids of two polypeptides which when optimally aligned have 95% amino acid identity. Preferably, residue positions which are not identical differ by conservative amino acid substitutions. For example, the substitution of amino acids having similar chemical properties such as charge or polarity are not likely to affect the properties of a protein. Examples include glutamine for asparagine or glutamic acid for aspartic acid.

As further applied to polypeptides, the terms "substantial homology" or "substantial sequence homology" mean that two peptide sequences, when optimally aligned, such as by the programs GAP or BESTFIT using default gap, share at least 90 percent sequence homology, preferably at least 95 percent sequence homology, more preferably at least 96, 97, 98 or 99 percent sequence homology.

"Percentage amino acid homology" or "percentage amino acid sequence homology" refers to a comparison of the amino acids of two polypeptides which, when optimally aligned, have approximately the designated percentage of the same amino acids or conservatively substituted amino acids. For example, "95% amino acid homology" refers to a comparison of the amino acids of two polypeptides which when optimally aligned have 95% amino acid homology. As used herein, homology refers to identical amino acids or residue positions which are not identical but differ only by conservative amino acid substitutions. For example, the substitution of amino acids having similar chemical properties such as charge or polarity are not likely to affect the properties of a protein. Examples include glutamine for asparagine or glutamic acid for aspartic acid.

The phrase "substantially purified" or "isolated" when referring to a protein (or peptide), means a chemical composition which is essentially free of other cellular components. It is preferably in a homogeneous state although it can be in either a dry or aqueous solution. Purity and homogeneity are typically determined using analytical chemistry techniques such as polyacrylamide gel electrophoresis or high performance liquid chromatography. A protein (or peptide) which is the predominant species present in a preparation is substantially purified. Generally, a substantially purified or isolated protein (or peptide) will comprise more than 80% of all macromolecular species present in the preparation. Preferably, the protein (or peptide) is purified to represent greater than 90% of all macromolecular species present. More preferably the protein (or peptide) is purified to greater than 95%, and most preferably the protein (or peptide) is purified to essential homogeneity, wherein other macromolecular species are not detected by conventional techniques. As used herein, a "substantially purified" or "isolated" protein (or peptide) can be synthetically or chemically produced, or recombinantly produced. A "substantially purified" or "isolated" protein or peptide as used herein is not intended to include a protein or peptide separated from an organism.

"Biological sample" or "sample" as used herein refers to any sample obtained from a living organism or from an organism that has died. Examples of biological samples include body fluids and tissue specimens.

High stringent hybridization conditions are selected at about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may significantly affect the stringency of hybridization, including, among others, base composition and size of the complementary strands, the presence of organic solvents, i.e. salt or formamide concentration, and the extent of base mismatching, the combination of parameters is more important than the absolute measure of any one. High stringency may be attained, for example, by overnight hybridization at about 68° C. in a 6×SSC solution, washing at room temperature with 6×SSC solution, followed by washing at about 68° C. in a 6×SSC solution then in a 0.6×SSX solution.

Hybridization with moderate stringency may be attained, for example, by: 1) filter pre-hybridizing and hybridizing with a solution of 3×sodium chloride, sodium citrate (SSC), 50% formamide, 0.1 M This buffer at pH 7.5, 5×Denhardt's solution; 2) pre-hybridization at 37° C. for 4 hours; 3) hybridization at 37° C. with amount of labeled probe equal to 3,000,000 cpm total for 16 hours; 4) wash in 2×SSC and 0.1% SDS solution; 5) wash 4× for 1 minute each at room temperature and 4× at 60° C. for 30 minutes each; and 6) dry and expose to film.

The phrase "selectively hybridizing to" refers to a nucleic acid molecule that hybridizes, duplexes or binds only to a particular target DNA or RNA sequence when the target sequences are present in a preparation of total cellular DNA or RNA. By selectively hybridizing it is meant that a nucleic acid molecule binds to a given target in a manner that is detectable in a different manner from non-target sequence under moderate, or more preferably under high, stringency conditions of hybridization. "Complementary" or "target" nucleic acid sequences refer to those nucleic acid sequences which selectively hybridize to a nucleic acid molecule. Proper annealing conditions depend, for example, upon a nucleic acid molecule's length, base composition, and the number of mismatches and their position on the molecule, and must often be determined empirically. For discussions of nucleic acid molecule (probe) design and annealing conditions, see, for example, Sambrook et al. 1989.

It will be readily understood by those skilled in the art and it is intended here, that when reference is made to particular sequence listings, such reference includes sequences which substantially correspond to its complementary sequence and those described including allowances for minor sequencing errors, single base changes, deletions, substitutions and the like, such that any such sequence variation corresponds to the nucleic acid sequence of the peptide/protein to which the relevant sequence listing relates.

The DNA molecules of the subject invention also include DNA molecules coding for protein analogs, fragments or derivatives of the protein which differ from naturally-occurring forms (the naturally-occurring protein) in terms of the identity or location of one or more amino acid residues (deletion analogs containing less than all of the residues specified for the protein, substitution analogs wherein one or more residues specified are replaced by other residues, and addition analogs wherein one or more amino acid residues are added to a terminal or medial portion of the protein) and which share the function of the naturally-occurring form. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

As used herein, a "peptide" refers to an amino acid sequence of three to one hundred amino acids, and therefore an isolated peptide that comprises an amino acid sequence is not intended to cover amino acid sequences of greater than 100 amino acids. Preferably, the peptides that can be identified and used in accordance with the subject invention (whether they be mimotope or anti-mimotope peptides) are less than 50 amino acids in length, and more preferably the peptides are five to 20 amino acids in length or 20–40 amino acids in length.

The peptides can contain any naturally-occurring or non-naturally-occurring amino acids, including the D-form of the amino acids, amino acid derivatives and amino acid mimics, so long as the desired function and activity of the peptide is maintained. The choice of including an (L)- or a (D)-amino acid in the peptides depends, in part, on the desired characteristics of the peptide. For example, the incorporation of one or more (D)-amino acids can confer increased stability on the peptide and can allow a peptide to remain active in the body for an extended period of time. The incorporation of one or more (D)-amino acids can also increase or decrease the pharmacological activity of the peptide.

The peptides may also be cyclized, since cyclization may provide the peptides with superior properties over their linear counterparts.

As used herein, the terms "amino acid mimic" and "mimetic" mean an amino acid analog or non-amino acid moiety that has the same or similar functional characteristic of a given amino acid. For instance, an amino acid mimic of a hydrophobic amino acid is one which is non-polar and retains hydrophobicity, generally by way of containing an aliphatic chemical group. By way of further example, an arginine mimic can be an analog of arginine which contains a side chain having a positive charge at physiological pH, as is characteristic of the guanidinium side chain reactive group of arginine.

In addition, modifications to the peptide backbone and peptide bonds thereof are also encompassed within the scope of amino acid mimic or mimetic. Such modifications can be made to the amino acid, derivative thereof, non-amino acid moiety or the peptide either before or after the amino acid, derivative thereof or non-amino acid moiety is incorporated into the peptide. What is critical is that such modifications mimic the peptide backbone and bonds which make up the same and have substantially the same spacial arrangement and distance as is typical for traditional peptide bonds and backbones. An example of one such modification is the reduction of the carbonyl(s) of the amide peptide backbone to an amine. A number of reagents are available and well known for the reduction of amides to amines such as those disclosed in Wann et al., JOC, 46:257 (1981) and Raucher et al., Tetrahedron. Lett., 21:14061 (1980). An amino acid mimic is, therefor, an organic molecule that retains the similar amino acid pharmacophore groups as is present in the corresponding amino acid and which exhibits substantially the same spatial arrangement between functional groups.

The substitution of amino acids by non-naturally occurring amino acids and amino acid mimics as described above can enhance the overall activity or properties of an individual peptide based on the modifications to the backbone or side chain functionalities. For example, these types of alterations to the amino acid substituents and peptides can enhance the peptide's stability to enzymatic breakdown and increase biological activity. Modifications to the peptide backbone similarly can add stability and enhance activity.

One skilled in the art, using the above sequences or formulae, can easily synthesize the peptides. Standard procedures for preparing synthetic peptides are well known in the art. The novel peptides can be synthesized using: the solid phase peptide synthesis (SPPS) method of Merrifield (J. Am. Chem. Soc., 85:2149 (1964)) or modifications of SPPS; or, the peptides can be synthesized using standard solution methods well known in the art (see, for example, Bodanzsky, M., Principles of Peptide Synthesis, 2nd revised ed., Springer-Verlag (1988 and 1993)). Alternatively, simultaneous multiple peptide synthesis (SMPS) techniques well known in the art can be used. Peptides prepared by the method of Merrifield can be synthesized using an automated peptide synthesizer such as the Applied Biosystems 431A-01 Peptide Synthesizer (Mountain View, Calif.) or using the manual peptide synthesis technique described by Houghten, Proc. Natl. Acad. Sci., USA 82:5131 (1985).

With these definitions in mind, the subject invention provides isolated nucleic acid molecules and proteins encoded by the isolated nuclei acid molecules. The proteins have transcriptional activation activity, i.e. they activate transcription. The nucleic acid molecules can be deoxyribonucleic acid (DNA) or ribonucleic acid (RNA, including messenger RNA or mRNA), genomic or recombinant, biologically isolated or synthetic.

An example of the protein is the protein encoded by the nucleotide sequence as shown in SEQ ID NO:1 (this is the open reading frame). The amino acid sequence encoded by this nucleotide sequence is shown in SEQ ID NO:3. The full nucleotide sequence is as shown in SEQ ID NO:2.

The invention also provides an oligonucleotide that is complementary to at least a portion of the mRNA encoding the protein. Oligonucleotides can be RNA or single-stranded DNA, and can be complementary to the entire mRNA molecule encoding the protein (i.e. of the same nucleotide length as the entire molecule). It may be desirable, however, to work with a shorter molecule. In this instance, the oligonucleotide can be complementary to a portion of the entire mRNA molecule encoding the protein. These shorter oligonucleotides are capable of hybridizing to the mRNA encoding the entire molecule, and preferably consist of about twenty to about one hundred nucleotides. These oligonucleotides can be used to reduce levels of proteins having transcriptional activating activity, by introducing into cells an RNA or single-stranded DNA molecule that is complementary to at least a portion of the mRNA of the protein (i.e. by introducing the oligonucleotide). The oligonucleotide can base-pair with the mRNA of the protein, preventing translation of the mRNA into protein. Thus, an oligonucleotide can prevent translation of mRNA encoding the protein into a functional protein. It may be desirable to place the oligonucleotide downstream and under the control of a particular promoter, so that the oligonucleotide will prevent translation of mRNA encoding the protein only in cells in which the particular promoter functions.

More particularly, an oligonucleotide complementary to at least a portion of mRNA encoding a transcriptional activator protein can be used to decrease expression of a functional channel. A cell with a first level of expression of a functional transcriptional activator protein is selected, and then the oligonucleotide is introduced into the cell. The oligonucleotide blocks expression of functional transcriptional activator protein, resulting in a second level of expression of a functional transcriptional activator protein in the cell. The second level is less than the initial first level.

Oligonucleotides can be introduced into cells by any suitable means. In one embodiment, the oligonucleotide RNA molecule is injected directly into the cellular cytoplasm, where the RNA interferes with translation. A vector may also be used for introduction of the oligonucleotide into a cell. Such vectors include various plasmid and viral vectors. For a general discussion of oligonucleotides such as antisense molecules and their use, see Han et al. 1991 and Rossi 1995.

The nucleic acid molecules of the subject invention can be expressed in suitable host cells using conventional techniques. Any suitable host and/or vector system can be used to express the transcriptional activator protein.

Techniques for introducing the nucleic acid molecules into the host cells may involve the use of expression vectors which comprise the nucleic acid molecules. These expression vectors (such as plasmids and viruses; viruses including bacteriophage) can then be used to introduce the nucleic acid molecules into suitable host cells. For example, DNA encoding the transcriptional activator protein can be injected into the nucleus of a host cell or transformed into the host cell using a suitable vector, or mRNA encoding the transcriptional activator protein can be injected directly into the host cell, in order to obtain expression of the transcriptional activator protein in the host cell.

Various methods are known in the art for introducing nucleic acid molecules into host cells. One method is microinjection, in which DNA is injected directly into the nucleus of cells through fine glass needles (or RNA is injected directly into the cytoplasm of cells). Alternatively, DNA can be incubated with an inert carbohydrate polymer (dextran) to which a positively charged chemical group (DEAE, for diethylaminoethyl) has been coupled. The DNA sticks to the DEAE-dextran via its negatively charged phosphate groups. These large DNA-containing particles stick in turn to the surfaces of cells, which are thought to take them in by a process known as endocytosis. Some of the DNA evades destruction in the cytoplasm of the cell and escapes to the nucleus, where it can be transcribed into RNA like any other gene in the cell. In another method, cells efficiently take in DNA in the form of a precipitate with calcium phosphate. In electroporation, cells are placed in a solution containing DNA and subjected to a brief electrical pulse that causes holes to open transiently in their membranes. DNA enters through the holes directly into the cytoplasm, bypassing the endocytotic vesicles through which they pass in the DEAE-dextran and calcium phosphate procedures. DNA can also be incorporated into artificial lipid vesicles, liposomes, which fuse with the cell membrane, delivering their contents directly into the cytoplasm. In an even more direct approach, DNA is absorbed to the surface of tungsten microprojectiles and fired into cells with a device resembling a shotgun.

Several of these methods, microinjection, electroporation, and liposome fusion, have been adapted to introduce proteins into cells. For review, see Mannino and Gould-Fogerite 1988, Shigekawa and Dower 1988, Capecchi 1980, and Klein et al. 1987.

Further methods for introducing nucleic acid molecules into cells involve the use of viral vectors. One such virus widely used for protein production is an insect virus, baculovirus. For a review of baculovirus vectors, see Miller (1989). Various viral vectors have also been used to transform mammalian cells, such as bacteriophage, vaccinia virus, adenovirus, and retrovirus.

As indicated, some of these methods of transforming a cell require the use of an intermediate plasmid vector. U.S. Pat. No. 4,237,224 to Cohen and Boyer describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture. The DNA sequences are cloned into the plasmid vector using standard cloning procedures known in the art, as described by Sambrook et al. (1989).

Host cells into which the nucleic acid encoding the transcriptional activator protein has been introduced can be used to produce the transcriptional activator protein.

Having identified the nucleic acid molecules encoding transcriptional activator proteins and methods for expressing the transcriptional activator proteins encoded thereby, the invention further provides methods of screening a substance (for example, a compound or inhibitor) for the ability of the substance to modify transcriptional activator protein function. In one embodiment, the method comprises introducing a nucleic acid molecule encoding the transcriptional activator protein into a host cell, and expressing the transcriptional activator protein encoded by the molecule in the host cell. The cell is then exposed to a substance and evaluated to determine if the substance modifies the function of the transcriptional activator protein. In another embodiment, an isolated transcriptional activator protein is exposed to the substance for evaluation of whether the substance modifies the function of the transcriptional activator protein. From these evaluations, substances effective in altering the function of the transcriptional activator protein can be found. Such agents may be agonists or antagonists, with antagonists being preferred herein.

The evaluation of a cell to determine if the substance modifies the function of the transcriptional activator protein can be by any means known in the art. The evaluation can comprise the direct monitoring of expression of transcriptional activator protein in the host cell, or the evaluation can be indirect.

The nucleic acid molecules of the subject invention can be used either as probes or for the design of primers to obtain DNA encoding other transcriptional activator proteins by either cloning and colony/plaque hybridization or amplification using the polymerase chain reaction (PCR).

Specific probes derived from SEQ ID NO:1 can be employed to identify colonies or plaques containing cloned DNA encoding a member of the transcriptional activator protein family using known methods (see Sambrook et al. 1989). One skilled in the art will recognize that by employing such probes under high stringency conditions (for example, hybridization at 42° C. with 5×SSPC and 50% formamide, washing at 50–65° C. with 0.5×SSPC), sequences having regions which are greater than 90% homologous or identical to the probe can be obtained. Sequences with lower percent homology or identity to the probe, which also encode transcriptional activator proteins, can be obtained by lowering the stringency of hybridization and washing (e.g., by reducing the hybridization and wash temperatures or reducing the amount of formamide employed).

More particularly, in one embodiment, the method comprises selection of a DNA molecule encoding a transcriptional activator protein, or a fragment thereof, the DNA molecule having a nucleotide sequence as shown in SEQ ID NO:1, and designing an oligonucleotide probe for transcriptional activator protein based on the nucleotide sequence of the selected DNA molecule. A genomic or cDNA library of an organism is then probed with the oligonucleotide probe, and clones are obtained from the library that are recognized by the oligonucleotide probe so as to obtain DNA encoding another transcriptional activator protein.

Specific primers derived from SEQ ID NO:1 can be used in PCR to amplify a DNA sequence encoding a member of the transcriptional activator protein family using known methods (see Innis et al. 1990). One skilled in the art will recognize that by employing such primers under high stringency conditions (for example, annealing at 50–60° C., depending on the length and specific nucleotide content of the primers employed), sequences having regions greater than 75% homologous or identical to the primers will be amplified.

More particularly, in a further embodiment the method comprises selection of a DNA molecule encoding transcriptional activator protein, or a fragment thereof, the DNA molecule having a nucleotide sequence as shown in SEQ ID NO:1, designing degenerate oligonucleotide primers based on the nucleotide sequence of the selected DNA molecule, and employing such primers in the polymerase chain reaction using as a template a DNA sample to be screened for the presence of transcriptional activator protein-encoding sequences. The resulting PCR products can be isolated and sequenced to identify DNA fragments that encode polypeptide sequences corresponding to the targeted region of transcriptional activator protein.

Various modifications of the nucleic acid and amino acid sequences disclosed herein are covered by the subject invention. These varied sequences still encode a functional transcriptional activator protein. The invention thus further provides an isolated nucleic acid molecule encoding a transcriptional activator protein, the nucleic acid molecule encoding a first amino acid sequence having at least 90% amino acid identity to a second amino acid sequence, the second amino acid sequence as shown in SEQ ID NO:3. In further embodiments, the first amino acid sequence has at least 95%, 96%, 97%, 98%, or 99% amino acid identity to SEQ ID NO: 3.

The invention further provides an isolated DNA oligomer capable of hybridizing to the nucleic acid molecule encoding the transcriptional activator protein according to the subject invention. Such oligomers can be used as probes in a method of detecting the presence of transcriptional activator protein in a sample. More particularly, a sample can be contacted with the DNA oligomer and the DNA oligomer will hybridize to any transcriptional activator protein present in the sample, forming a complex therewith. The complex can then be detected, thereby detecting presence of transcriptional activator protein in the sample.

The complex can be detected using methods known in the art. Preferably, the DNA oligomer is labeled with a detectable marker so that detection of the marker after the DNA oligomer hybridizes to any transcriptional activator protein in the sample (wherein non-hybridized DNA oligomer has been washed away) is detection of the complex. Detection of the complex indicates the presence of transcriptional activator protein in the sample. As will be readily apparent to those skilled in the art, such a method could also be used quantitatively to assess the amount of transcriptional activator protein in a sample.

For detection, the oligomers can be labeled with, for example, a radioactive isotope, biotin, an element opaque to X-rays, or a paramagnetic ion. Radioactive isotopes are commonly used and are well known to those skilled in the art. Representative examples include indium-111, technetium-99m, and iodine-123. Biotin is a standard label which would allow detection of the biotin labeled oligomer with avidin. Paramagnetic ions are also commonly used and include, for example, chelated metal ions of chromium (III), manganese (II), and iron (III). When using such labels, the labeled DNA oligomer can be imaged using methods known to those skilled in the art. Such imaging methods include, but are not limited to, X-ray, CAT scan, PET scan, NMRI, and fluoroscopy. Other suitable labels include enzymatic labels (horseradish peroxidase, alkaline phosphatase, etc.) and fluorescent labels (such as FITC or rhodamine, etc.).

The invention further provides an isolated transcriptional activator protein. The protein is preferably encoded by a nucleotide sequence as shown in SEQ ID NO:1. The protein preferably has an amino acid sequence as shown in SEQ ID NO:3. Further provided is an isolated transcriptional activator protein encoded by a first amino acid sequence having at least 90% amino acid identity to a second amino acid sequence, the second amino acid sequence as shown in SEQ ID NO:3. In further embodiments, the first amino acid sequence has at least 95%, 96%, 97%, 98%, or 99% amino acid identity to SEQ ID NO: 3.

The invention further provides an antibody or fragment thereof specific for the transcriptional activator protein of the subject invention. Antibodies of the subject invention include polyclonal antibodies and monoclonal antibodies capable of binding to the transcriptional activator protein, as well as fragments of these antibodies, and humanized forms. Humanized forms of the antibodies of the subject invention may be generated using one of the procedures known in the art such as chimerization. Fragments of the antibodies of the present invention include, but are not limited to, the Fab, the F(ab')$_2$, and the Fc fragments.

The invention also provides hybridomas which are capable of producing the above-described antibodies. A hybridoma is an immortalized cell line which is capable of secreting a specific monoclonal antibody.

In general, techniques for preparing polyclonal and monoclonal antibodies as well as hybridomas capable of producing the desired antibody are well known in the art (see Campbell 1984 and St. Groth et al. 1980). Any animal (mouse, rabbit, etc.) which is known to produce antibodies can be immunized with the antigenic transcriptional activator protein (or an antigenic fragment thereof). Methods for immunization are well known in the art. Such methods include subcutaneous or intraperitoneal injection of the protein. One skilled in the art will recognize that the amount of the protein used for immunization will vary based on the animal which is immunized, the antigenicity of the protein, and the site of injection.

The protein which is used as an immunogen may be modified or administered in an adjuvant in order to increase the protein's antigenicity. Methods of increasing the antigenicity of a protein are well known in the art and include, but are not limited to, coupling the antigen with a heterologous protein (such as a globulin or beta-galactosidase) or through the inclusion of an adjuvant during immunization.

For monoclonal antibodies, spleen cells from the immunized animals are removed, fused with myeloma cells, such as SP2/0-Ag 15 myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al. 1988).

Hybridomas secreting the desired antibodies are cloned and the class and subclass are determined using procedures known in the art (Campbell 1984).

For polyclonal antibodies, antibody containing antisera is isolated from the immunized animal and is screened for the presence of antibodies with the desired specificity using one of the above-described procedures.

In accordance with the above discussion, the subject invention further provides a method of producing an antibody specific for a transcriptional activator protein in a host. The method comprises selecting the isolated transcriptional activator protein or an antigenic portion thereof and introducing the selected transcriptional activator protein or antigenic portion thereof into a host to induce production of an antibody specific for transcriptional activator protein in the host.

The present invention further provides the above-described antibodies in detectably labeled form. Antibodies can be detectably labeled through the use of radioisotopes, affinity labels (such as biotin, avidin, etc.), enzymatic labels (such as horseradish peroxidase, alkaline phosphatase, etc.), fluorescent labels (such as FITC or rhodamine, etc.), paramagnetic atoms, etc. Procedures for accomplishing such labeling are well known in the art, for example see Sternberger et al. 1970, Bayer et al. 1979, Engval et al. 1972, and Goding 1976.

The labeled antibodies or fragments thereof of the present invention can be used for in vitro, in vivo, and in situ assays to identify cells or tissues which express transcriptional activator protein, to identify samples containing transcriptional activator protein, or to detect the presence of transcriptional activator protein in a sample. More particularly, the antibodies or fragments thereof can thus be used to detect the presence of transcriptional activator protein in a sample, by contacting the sample with the antibody or fragment thereof. The antibody or fragment thereof binds to any transcriptional activator protein present in the sample, forming a complex therewith. The complex can then be detected, thereby detecting the presence of transcriptional activator protein in the sample. As will be readily apparent to those skilled in the art, such a method could also be used quantitatively to assess the amount of transcriptional activator protein in a sample. As should also be readily apparent, such an antibody may also be used to decrease levels of functional transcriptional activator protein, by blocking the protein.

EXAMPLE

A subtractive hybridization protocol was used to identify novel expressed sequence tags (ESTs) corresponding to mRNAs whose expression was induced upon exposure of the human leukemia cell line K562 to the phorbol ester 12-O-tetradecanolyphorbol-13-acetate (TPA).

The complete open reading frame of one of the novel ESTs, named TIG-1, was obtained by screening K562 cell and placental cDNA libraries. The deduced open reading frame of the TIG-1 cDNA encodes for a glutamine repeat rich protein with a predicted molecular weight of 63 kDa. The predicted open reading frame also contains a consensus bipartite nuclear localization signal, though no specific DNA binding domain was found.

The corresponding TIG-1 mRNA is ubiquitously expressed. Placental tissue expresses the TIG-1 mRNA 200 fold times more than the lowest expressing tissues such as kidney and lung. There is also preferential TIG-1 RNA-expression in cells of bone marrow lineage.

In vitro transcription/translation of the TIG-1 cDNA yielded a polypeptide with an apparent molecular weight of 97 kDa. Using polyclonal antibodies obtained from a rabbit immunized with the carboxy terminal portion of bacterially expressed TIG-1 protein, a polypeptide with molecular weight of 97 kDa was identified by Western blot analyses of protein lysates obtained from K562 cells.

Cotransfection assays of K562 cells, using a GAL4-TIG-1 fusion gene and GAL4 operator-CAT, indicate that the TIG-1 protein may have transcriptional regulatory activity when tethered to DNA. It was hypothesized that this novel glutamine rich protein participates in a protein complex that regulates gene transcription. It has been demonstrated by Naar et. al., 1999 that the amino acid sequences of peptide fragments obtained from a polypeptide found in a complex of proteins that alters chromatin structure (ARC) are identical to portions of the deduced open reading frame of TIG-1 mRNA.

The K562 human leukemia cell line can be made to differentiate to a variety of myeloid derived lineages. Induction with hemin leads to expression of markers of erythroid differentiation, while exposure to the phorbol ester 12-O-tetradecanolyphorbol-13-acetate (TPA) leads to extinction of the erythroid phenotype and induction of a megakaryocytic phenotype. Previous work in many laboratories, has identified a set of erythroid specific genes, such as the globins and glycophorin A, whose expression was increased upon hemin induction of K562 cells (Andersson et. al., 1979, Charnay and Maniatis, 1983, Dean et. al., 1983). Gene expression during TPA induced megakaryocytic differentiation of K562 cells has been less well studied (Alitalo et. al. 1988, Alitalo et. al. 1990, Lin et al. 1994, Lumelsky and Forget, 1991).

Since the K562 cell line can serve as a model for pluripotent bone marrow stem cell differentiation; it is of interest to identify novel genes preferentially expressed in myeloid lineage cells. Subtractive hybridization protocol, first introduced by Wang and Brown, was used to identify cDNAs corresponding to novel mRNAs whose expression was increased after K562 cell induction with TPA.

The molecular cloning, expression, and functional characterization of TIG-1, a novel human CAG repeat rich cDNA, whose corresponding mRNA contains a deduced open reading frame encoding for a glutamine repeat rich protein with a consensus bipartite nuclear localization signal is reported. The 3.7 kb mRNA encoding for this protein, though constitutively expressed, is highly preferentially expressed in placental and bone marrow lineage cells. Using rabbit polyclonal antibodies raised to the bacterially expressed carboxy terminal portion of the deduced open reading frame of TIG-1, Western blot analyses of K562 cell protein extracts show that TIG-1 is found in the cytoplasm and nucleus with an apparent molecular weight of 97 kDa.

In transient transfection assays of K562 cells transfected with a GAL4:TIG-1 fusion gene in an eukaryotic expression vector, evidence is presented that the protein encoded by this novel cDNA has transcriptional regulatory activity when tethered to DNA by the Gal 4 DNA binding domain.

Material and Methods

Cell Culture:

K562 cells were grown in RPMI 1640 medium supplemented with 10% heat inactivated fetal bovine serum and incubated at 37° C. in the presence of 5% $CO_2$. Cells were induced with 20 $\mu$M hemin for 48 hours or 34 nM TPA for 72 hours.

Construction of Expressed Sequence Tag Library by Subtraction of Hemin Induced cDNAs from TPA Induced cDNAs Derived from mRNAs Obtained from K562 Cells:

Poly $A^+$ mRNAs were isolated from K562 cells induced with either 20 $\mu$M hemin for 72 hours or 34 nM TPA for 48 hours. The corresponding cDNAs were synthesized using a cDNA construction kit (Amersham, Chicago, Ill.).

The protocol elaborated by Wang and Brown 1991 with some modification. Long cDNAs were digested with the restriction endonuclease Rsa 1 and then ligated to linker DNAs (SEQ ID NO:7: 5'GAATTCAGATCTCCCGGGT-CACCGC3' and SEQ ID NO:8: 5'TGACCCGGGAGATCGAATTC3'). Linkered cDNA fragments were amplified by PCR. PCR amplified cDNA fragments constructed from the TPA induced mRNAs were used as "tracer" cDNAs, while a five fold molar excess of biotinylated PCR amplified cDNA fragments constructed from hemin induced mRNAs were used as "driver" cDNAs to produce a EST library that was highly enriched in cDNA fragments generated from the TPA induced K562 cells.

The subtractive hybridization reaction was performed as follows:

10 μg of cDNA fragments produced from hemin induced K562 mRNAs were mixed with 10 μg of photoprobe bictin™ (Vector Laboratories, Burlingame, Calif.) kept on ice and was exposed to a 270 Watt sunlamp kept 10 cm above the mixture for 15 minutes. The biotinylation procedure was performed a second time. The reaction was then stopped by neutralization with an equal volume of 0.1 M Tris HCl (pH 9.0) and the final volume was adjusted to 100 μl with distilled water.

Unreacted biotin species were then extracted with the addition of an equal volume of 2-Butanol and the extraction was repeated twice. The aqueous phase containing the biotinylated DNA was precipitated with 1/10 volume of 1 M NaCl and 2 Volumes of ethanol. The biotinylated cDNA pool was resuspended in 10 μl of Tris:EDTA (pH 7.6).

5 μg of biotinylated cDNA "driver" fragments produced from hemin induced mRNAs were mixed with 1 μg of "tracer" cDNA fragments produced from TPA induced K562 mRNAs and precipitated with ethanol; then resuspended in 20 μl of TE pH 8.0. This mixture was denatured by boiling in a water bath for 3 minutes, centrifuged briefly and then an equal volume of 2×hybridization buffer (50 mM HEPES (pH 7.5), 2 mM EDTA, 1.5 M NaCl) was added and overlaid with mineral oil. The hybridization mixture was denatured again in a boiling water bath for 3 minutes and then hybridized for 2 hours at 63° C.

The hybridization reaction was stopped with the addition of 160 μL of HE buffer solution (10 mM HEPES, 1 mM EDTA pH 7.6 prewarmed to 55° C.) and the aqueous phase transferred to an eppendorf tube prewarmed at 55° C. for five minutes. The biotinylated cDNAs were complexed by the addition of 5 μL of streptavidin solution (10 mg/ml of streptavidin in 0.15 M NaCl, 10 mM HEPES pH 7.6, 1 mM EDTA) and the reaction mix was incubated at room temperature for 20 minutes. The streptavidin:biotin complex was extracted with equal volumes of phenol:chloroform (1:1) prewarmed to 37° C. Phenol:chloroform extractions were repeated until no visible DNA complex was noted at interphase. Then the aqueous phase containing the remaining subtracted cDNAs was extracted with chloroform, ethanol precipitated and resuspended in 20 μL of TE (pH 8.0).

The entire procedure described above was repeated using the subtracted cDNAs obtained from the short hybridization reaction as "tracer", with the remaining biotinylated driver cDNA fragments; but this time the hybridization mixture was hybridized for 24 hours at 63° C.

The subtracted cDNAs enriched for cDNAs derived from TPA induced K562 mRNAs were then amplified by PCR for thirty cycles (94° C. 1 minute, 50° C. 1 minute, 72° C. 3 minutes). The resultant amplified enriched cDNA pool was then digested with the restriction endonuclease EcoR1, ligated into the plasmid Bluescript pBS KS II+, and transformed into XL-blue 1 cells by electroporation. Transformed cells were plated to produce the expressed sequence tag library enriched for inserts derived from TPA induced K562 cell mRNAs.

Expressed Sequence Tag Library Sequence Analysis

Expressed sequence tag inserts in the plasmid pBS KS+ were flanked by the T3 and T7 promoters. Inserts were directly sequenced using T3 or T7 sequencing primers. Sequence analysis of the inserts was performed on GenBank, EMBL, PIR, and Swissprot databases using FASTA and BLAST algorithms.

Screening of cDNA Libraries

The 193 bp EST fragment from clone pSA25 was used as a probe to screen K562 or placental cell 1 GT11 cDNA libraries. Using standard screening techniques we identified a K562 cell clone that contained a 1.5 kb insert which contained the 193 bp sequence of the screening probe. This 1.5 kb cDNA fragment was used to screen the placental phage clones and identified individual clones containing 2.1 and 2.5 kb of cDNA sequence. DNA sequences of these partial cDNAs were obtained by manual and automated sequencing.

Northern Blots:

Total RNA was isolated from uninduced, hemin, or TPA induced K562 cells with TRI reagent (Molecular Research Center, Inc., Cincinnati, Ohio) according to the manufacturer's protocol. Twenty μg of total RNA was size fractionated in a 1.5% formaldehyde agarose gel. The RNA was transferred onto a nylon membrane overnight by capillary action. The nylon membrane was washed briefly in 6×SSC and then UV cross-linked. Membranes were stored at 4° C. Multiple organ and immune tissue blots were purchased from Clontech laboratories (Palo Alto, Calif.).

All blots were probed with the 193 bp EST fragment of TIG-1. Expression of TIG-1 mRNA in K562 cell Northern blots was normalized to expression of G3PDH mRNA; for blots obtained from Clontech, expression of TIG-1 was normalized to expression of β-actin MRA.

In Vitro Transcription and Translation

A plasmid containing 3.2 kb of the TIG-1 cDNA was linearized by restriction enzyme digestion and then transcribed with either T7 or T3 RNA polymerase to generate sense or antisense transcripts. Transcripts produced in vitro were analyzed on a 1.5% formaldehyde agarose gel.

A rabbit reticulocyte lysate obtained from Promega (Madison, Wis.) was used for the in vitro translation reaction. In vitro translation products were analyzed on a 10% SDS-polyacrylamide gel that was stained with Coomassie Blue.

Production of Antibodies to the Carboxy Terminal Portion of the TIG-1 Protein

PCR primers were used to amplify the coding region of TIG-1 protein from amino acids 394 to 579. This fragment was cloned in frame 3' to the coding sequence for glutathione S-transferase (GST). The resultant plasmid was transformed into E. coli which were grown and induced with 0.5 mM IPTG to overexpress the GST:TIG-1 fusion protein. This protein was affinity purified with glutathione agarose beads following the manufacturers directions. Confirmation that a GST fusion protein was obtained by performing a Western Blot using a monoclonal antibody directed to the GST portion of the fusion protein. A fusion protein of the correct expected molecular weight was detected.

The GST:TIG-1 fusion protein was used to immunize a rabbit (CoCalico Biologics, Reamstown, Pa.). Antiserum was obtained six weeks, 12, and 18 weeks after the first injection of the protein.

Affinity Purification of TIG-1 Antiserum

One ml of post immune serum was incubated with GST protein at 4° C. overnight. The reaction was then centrifuged at 3000 rpm for 5 minutes and the supernatant was transferred to a fresh tube. This supernatant was incubated at 4° C. for 12 hours with a nitrocellulose membrane which contained the 46 kDa GST:TIG-1 fusion protein transferred to the nitrocellulose membrane following SDS-PAGE electrophoresis. The membrane was washed in PBS at room temperature for 15' repeated ×3; then affinity purified antibody was eluted from the membrane by addition of elution buffer (0.1 M glycine, 0.1 M NaCl pH 2.5) and shaking at room temperature for 20'. The eluate was transferred to a fresh tube and neutralized with 1 M Tris pH 8.8 to a pH of 7.5. Bovine serum albumin (BSA) was added to a final concentration of 5 mg/ml. The affinity purified antibodies were stored at 4° C. till further use.

Western Blot Analyses of K562 Cytoplasmic and Nuclear Extracts with Affinity Purified Antibodies:

Nuclear extracts were made from uninduced, hemin, and TPA induced K562 cells using the Dignam protocol (Dignam et. al. 1983). Cytoplasmic extracts were obtained following Dounce homogenization and centrifugation to produce the nuclear pellet. Cytoplasmic and Dignam nuclear extracts were stored at −70° C. till further use.

50 μg aliquots of protein from the cytoplasmic or nuclear extracts were size fractionated on a 10% SDS-PAGE gel and transferred to a nitrocellulose membrane. Membranes were incubated for 1 hour at room temperature with either a 1:100 dilution of preimmune serum or 1:5 dilutions of affinity purified pre- or post-immune serum. The membrane was washed and incubated with goat antirabbit antibody followed by a chemi-luminscent reaction used to identify protein bands that were specifically recognized by post-immune serum.

Transient Transfection Experiments

5×10$^7$ cells were used for each transfection. All transfections contained 5 μg of the reporter plasmid pGALx5OP E1B CAT, 2 μg of pCMVβ gal (to assay for transfection efficiency), and a test plasmid in either a 1:1 or 1:5 molar ratio with the reporter plasmid. Plasmid DNAs were transiently transfected into K562 cells via electroporation at 250V and 960 μF with a Bio-Rad (Hercules, Calif.) Gene pulser. After resting on ice for 30 minutes, each electroporation reaction was resuspended in 10 ml of fresh RPMI 1640 medium and incubated for 12 hours at 37° C. Then each dish of transfected cells was split into three equal volumes and replated using either TPA or hemin as an inducing agent.

Forty eight hours after transient transfection whole cell freeze-thaw lysates were prepared and stored till further use at −20° C. Protein concentration of lysates were measured with the Bradford Reagent. Equal amounts of protein lysates from each dish of transfected cells was used to measure β-gal and CAT protein activities via standard techniques.

Results and Discussion

Figures 1A, 1B:
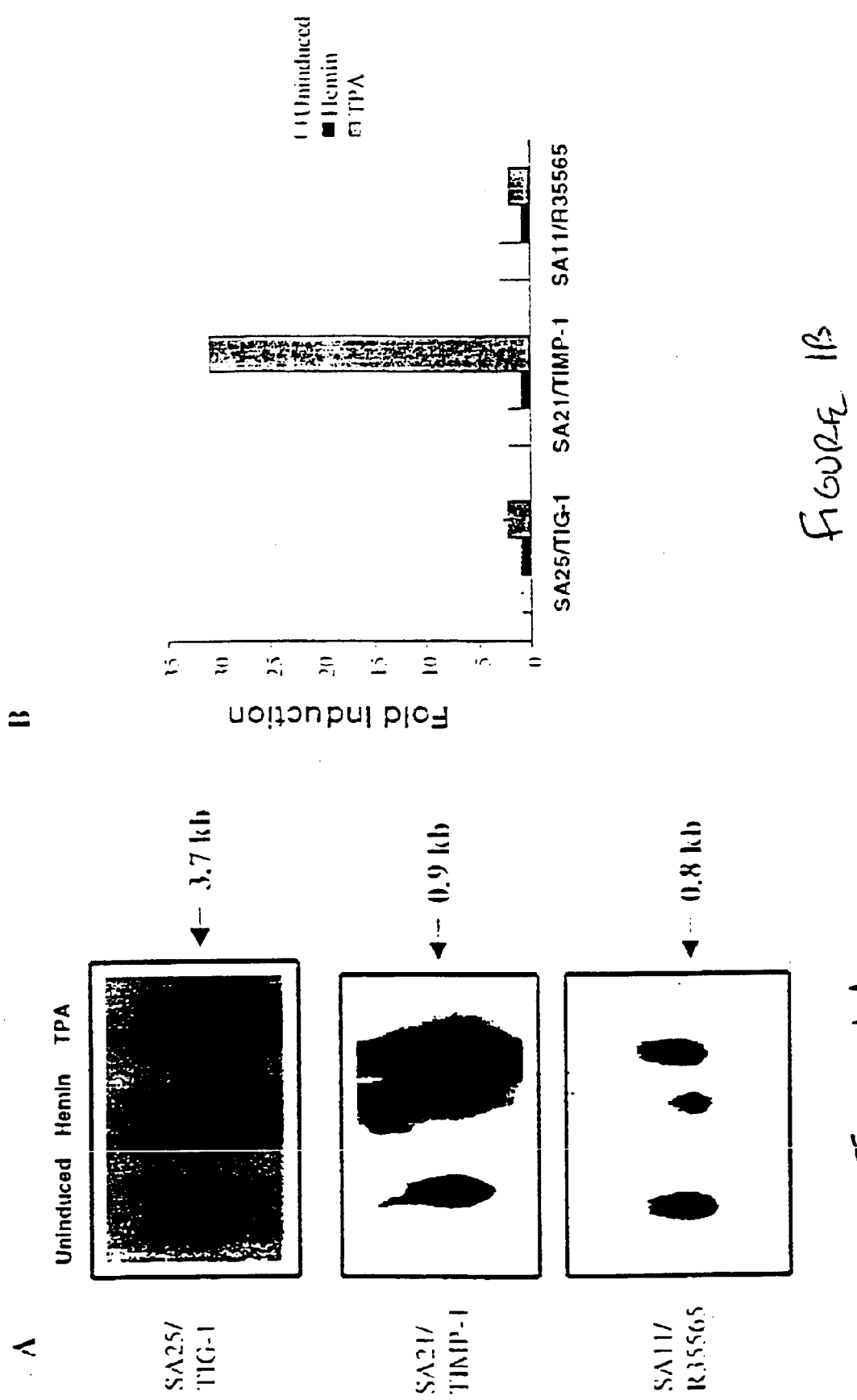
FIGS. 1A and B show a Northern Blot Analyses of Total Cellular RNA obtained from uninduced, hemin, or TPA induced K562 cells.
FIG. 1B: Fold induction of TIG-1, TIMP-1, and R35565 mRNAs with mRNAs obtained from hemin induced K562 cells taken as 1. Amounts of mRNA expression were normalized to G3PDH mRNA expression under each inducing condition.

Identification of Expressed Sequence Tag Fragments Corresponding to TPA Induced mRNAs Following two rounds of subtractive hybridization, the recombinant cDNA clones were isolated and their sequences searched for possible homology to genes in the NIH database. To confirm that the subtractive hybridization yielded cDNA clones corresponding to mRNAs whose expression increased following TPA induction of K562 cells, the expression of three randomly picked clones: SA11, SA21, and SA25 was analyzed by Northern blot. The expression of mRNAs hybridizing to each of these clones was found to be upregulated following 72 hours of TPA induction of K562 cells as shown in FIG. 1A. These three independent cDNA fragments hybridized to 0.8 kb, 0.9 kb, and 3.7 kb mRNA transcripts, respectively.

The cDNA fragment (SA21) was found to be identical to a partial sequence for the tissue inhibitor of metalloproteinases gene-1 (Alitalo et. al. 1990) which showed (in comparison to hemin-induced mRNA levels) a 30-fold TPA induced mRNA increase (FIG. 1B: SA21/TIMP-1). The sequence of the cDNA SA11 corresponding to a 0.8 kb mRNA was found to be identical to an EST in the database of unknown function. This 0.8 kb mRNA demonstrated (in comparison to hemin induced levels) a 1.5 fold TPA induced increase.

The 193 bp cDNA fragment SA25, which hybridized to a 3.7 kb mRNA, was not identical to any sequence in the NIH database. This novel cDNA was named TPA inducible gene 1 (TIG-1). The 3.7 kb TIG-1 mRNA demonstrated (in comparison to hemin induced levels) a 2.5 fold TPA induced increase (FIG. 1B: SA25/TIG-1). On the basis of this Northern blot analysis we believe that the subtractive library represents genes expressed during TPA induction of K562 cells.

Figure 2B:
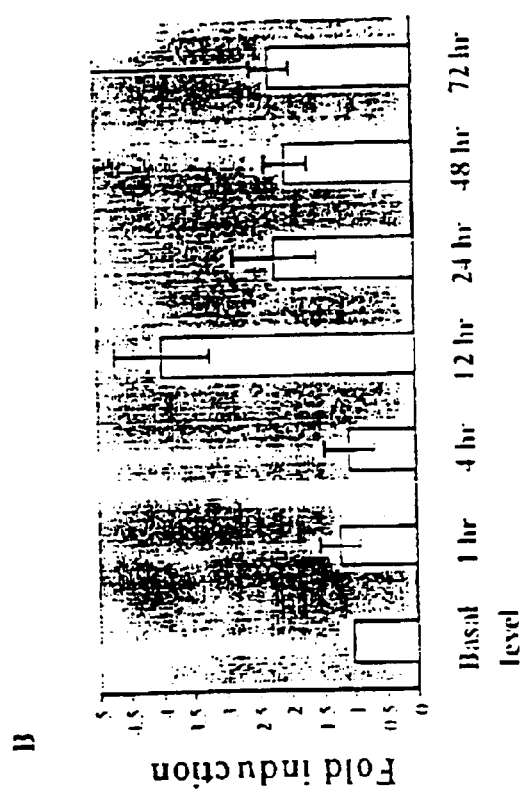
FIG. 2B: Bar graph of fold induction of TIG-1 mRNA at various time points after TPA induction of K562 cells. Fold induction was normalized to expression of G3PDH mRNA at each time point.
Figure 2A:
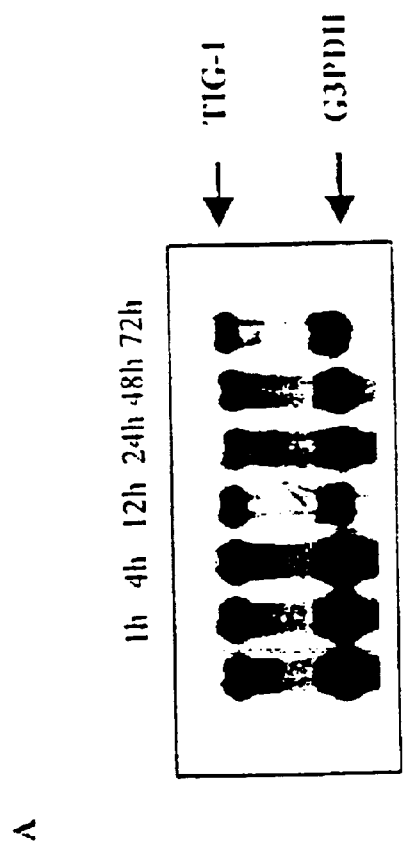
FIGS. 2A and B show a Northern Blot Analysis of TPA induced K562 mRNA demonstrating time course of TIG-1 mRNA expression.

3.2. Time Course of TPA Induction of K562 Cells on Expression of TIG-1 mRNA:

To determine whether there was a change in the steady state level of TIG-1 mRNA with shorter periods of TPA induction, total cellular RNA isolated from K562 cells was analyzed at 1 hr, 4 hrs, 12 hrs, 24 hrs, 48 hrs and 72 hrs after induction with TPA. Northern blots were probed with a TIG-1 cDNA fragment. The steady state level of TIG-1 mRNA was found to vary, with a 3.5–4 fold induction at 12 hrs in TPA induced cells in comparison to uninduced cells. The expression then declined to a 2–2.5-fold induction over 72 hrs. An increase in the steady state level of TIG-1 mRNA occurs between 4–12 hrs following TPA induction (FIG. 2A and 2B). Whether there is a cell cycle stage dependency on the level of TIG-1 mRNA expression remains to be determined. The K562 cells were not synchronized prior to induction with TPA.

Expression of TIG-1 mRNA in Various Tissues

Figures 3A, 3B:
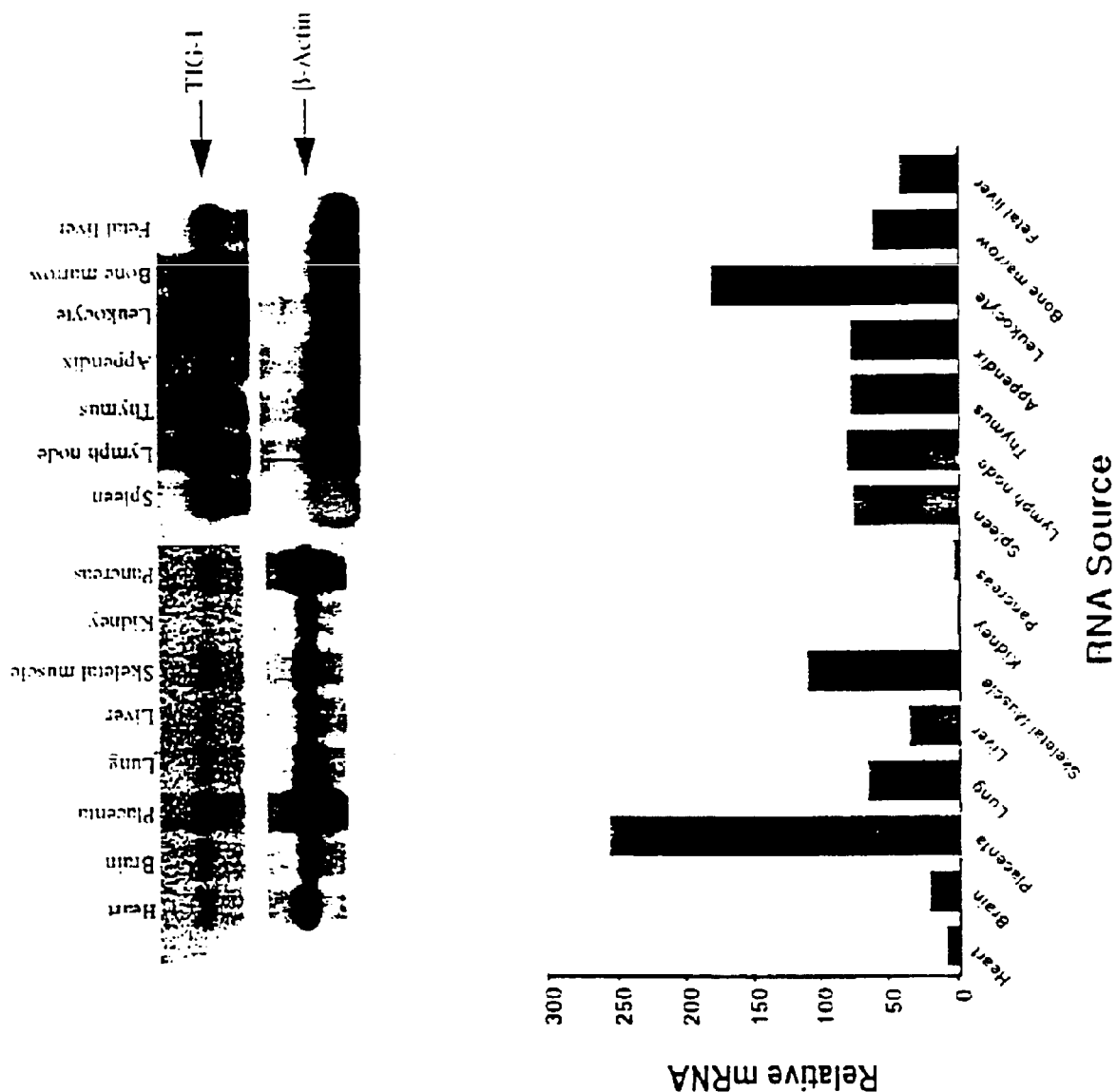
FIGS. 3A and B shows a Northern Blot Analysis of the expression of TIG-1 mRNA in various tissues.
FIG. 3B: Bar graph showing relative expression of TIG-1 mRNA in each tissue with 1 taken as level of expression in the kidney. Each bar represents the average of two independent determinations of TIG-1 expression. TIG-1 mRNA expression was normalized to β-actin mRNA expression in each tissue.

Northern blot analyses was used to determine whether the mRNA encoding TIG-1 exhibited any tissue restricted pattern of expression. Screening was used to detect the presence of human TIG-1 mRNA in hematopoietic and non-hematopoietic tissues. Using the 193 bp TIG-1 cDNA fragment as a probe, a 3.7 kb transcript was detected in all tissues examined, as shown in FIG. 3A. The wide range of tissues expressing TIG-1 mRNA suggests that the protein encoded by this mRNA serves a constitutive function in the cell. However, the level of TIG-1 mRNA expression varied; with the highest amounts of expression in the placenta and peripheral blood leukocytes, and lowest in the pancreas and the kidney (FIG. 3B). In comparison to the kidney, there was 250 times more expression of TIG-1 mRNA in the placenta and fifty times more expression in bone marrow derived tissues (FIG. 3B). Whether there is the same wide variability in the level of TIG-1 protein expression between tissues remains to be determined.

Determination of the Full Length cDNA Sequence of TIG-1

Full length K562 cell and placental cDNA libraries were screened in order to obtain approximately 3.4 kb of nucleotide sequence. This contig contained 163 bp of 5' untranslated region, a 1,737 bp open reading frame encoding for 579 amino acids, and 1,499 bp of 3' untranslated region.

Figure 4:
FIG. 4 illustrates the sequence of the TIG-1 cDNA.

The proximal ATG codon begins at 164 bp from the start base pair of the 3.4 kb contig, and is preceded by the Kozak sequence GCC<u>ATG</u>A in an adequate context, predicting a continuous open reading frame (ORF) of 1737 bp as shown in FIG. 4. A putative polyadenylation signal AATAAA is located 16 bp upstream of the poly A tail and is underlined. The complete predicted ORF of the TIG-1 cDNA sequence encodes a protein of 579 amino acids with a predicted molecular weight of 63 kDa. The deduced protein has an isoelectric pH of 10.0 and is rich in glutamine (28%), serine (10%) and proline residues (17%). The deduced amino acid sequence shows seven glutamine rich repeat regions containing homopolymeric repeats of 6–16 glutamine residues, as shown in FIG. 5. A putative bipartite nuclear localization signal was identified at amino acid residues 515–525 (FIG. 5.).

While the full length sequence of TIG-1 cDNA was being determined, a partial cDNA fragment CTG7a was found in the database which was identical to the TIG-1 cDNA corresponding to amino acids 160–525 of the deduced open reading frame. This partial cDNA fragment was obtained by Ross et. al. 1997 following a screen of a brain cDNA library with a CAG repeat oligonucleotide in hopes of identifying novel genes involved in neurological disorders that are subject to trinucleotide expansion repeat mutations. Expression of TIG-1 mRNA in brain tissue is demonstrated in FIG. 3A.

In Vitro Transcription and Translation of TIG-1 cDNA

To determine whether the TIG-1 cDNA clone could produce a mRNA transcript that yielded a polypeptide of the predicted 63 kDa size, in vitro transcription and translation of TIG-1 cDNA was carried out. Linearized TIG-1 cDNA was transcribed by T3 RNA polymerase or T7 RNA polymerase, to generate antisense or sense transcripts respectively. These transcripts were then translated in vitro by a rabbit reticulocyte lysate system. The $^{35}S$ methionine labeled translated products were fractionated on a 10% SDS-PAGE gel. Translation of the sense transcripts produced a polypeptide of approximately 97 kDa and smaller polypeptides as seen in FIG. 6A, lane 4. It is possible that the smaller polypeptides arise from incomplete translational products or are due to proteolytic degradation. Antisense transcripts failed to produce any polypeptide (FIG. 6A, lane 5). No polypeptide bands were detected following in vitro translation of mRNA transcripts produced from a DNA template of the Bluescript plasmid (FIG. 6A, lane 6) or with a TIG-1 cDNA template (FIG. 6A, lane 1). The control, p45NF-E2 sense transcripts, yielded a 45 kDa polypeptide (FIG. 6A, lane 2) while no translation products were detected with p45 NF-E2 antisense transcripts (FIG. 6A, lane 3).

Detection of TIG-1 Protein in K562 Cells:

To detect TIG-1 protein in K562 cells, an immuno-affinity purified rabbit polyclonal antibody was used to the carboxy terminal portion of bacterially expressed TIG-1 protein in Western Blot analyses of cytosolic and nuclear extracts obtained from K562 cells. The affinity purified post-immune serum detected a protein of 97 kDa in the nuclear and cytoplasmic extracts of uninduced K562 cells, as shown in FIG. 6B, lanes 5 and lanes 6. No protein bands were detected with pre-immune serum (FIG. 6B, lanes 1, 2, 3, and 4). Similarly, the 97 kDa TIG-1 protein was detected in TPA-induced K562 cells with affinity-purified post immune serum (data not shown).

Western blot analyses of K562 protein lysates using affinity-purified antiserum preincubated with either bacterially expressed TIG-1 carboxy terminal peptide or bovine serum albumin confirmed the specificity of the antiserum. The 97 kDa TIG-1 protein band could not be detected by the affinity purified TIG-1 antiserum when it was preincubated with the TIG-1 carboxy terminal peptide; while the 97 kDa polypeptide band was observed when bovine serum albumin was preincubated with the affinity purified TIG-1 antiserum (data not shown).

Though the deduced open reading frame of the TIG-1 cDNA predicts a polypeptide of MW 63 kDa both the in vitro transcription and translation data shown in FIG. 6A, and the Western Blot analysis shown in FIG. 6B demonstrate a protein product of MW 97 kDa. It is possible that the difference between the predicted and the observed MW of the TIG-1 protein is due to anomalous migration of a glutamine rich protein as observed by Cox et. al. 1996, or due to the high positive charge of the TIG-1 protein with a predicted pI of 10.0.

CAT Assay for Detection of Possible Transcription Regulatory Activity of GAL4-TIG-1 Fusion Protein Though the deduced ORF of TIG-1 showed a putative consensus nuclear localization signal, no putative DNA binding domain was found. To determine whether the TIG-1 protein had any possible effect on activation of transcription cotransfection assays using a cat reporter vector and an expression vector encoding for the full length TIG-1 protein fused 3 minutes to DNA binding domain of GAL4 protein (GAL4-TIG-1). The cat reporter construct contained five GAL4 binding sites 5' to the minimal promoter for the adenovirus E1B gene, pGAL4$_5$E1BCAT (FIG. 7A). Expression of the GAL4-TIG-1 fusion plasmid would result in the tethering of TIG-1 protein to DNA via the DNA binding domain of GAL 4.

The GAL4-TIG-1 expression plasmid cotransfected in the molar concentration of 1:5 to the CAT reporter plasmid showed a 3-fold increase in CAT expression in uninduced K562 cells, when compared to the CAT activity of the Gal4 DNA binding domain taken as 1 (data not shown). This suggests that TIG-1 protein could behave as a transcriptional activator. It was asked whether the glutamine rich domain of TIG-1 protein was sufficient for transcriptional activation (Gerber et. al. 1994). The construct GAL4-GLU which encodes for the glutamine rich portion of TIG-1 did not show any transactivation activity (FIG. 7B and 7C, GAL4-Glu). It was verified that this fusion construct was indeed expressed by performing electrophoretic mobility shift analysis of nuclear extracts obtained from K562 cells transfected with this construct and a radiolabelled oligonucleotide robe containing the GAL4 operator sequence. The GAL4 operator probe was shifted by a GAL4:GLU fusion protein indicating that this fusion protein was made (data not shown). The reporter vector pGAL4$_5$E1BCAT transfected in the absence of GAL4-TIG-1 or with the expression vector for the GAL 4 DNA binding domain did not produce any cat gene expression (FIG. 7B and 7C: neg and GAL4).

Figure 7:
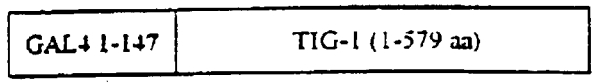
Figure 7:
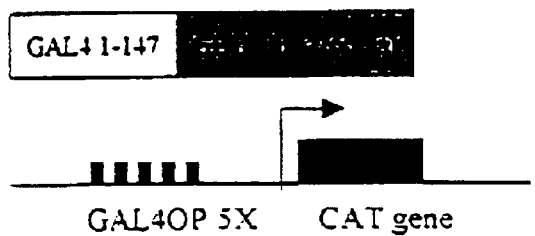
Figure 7:
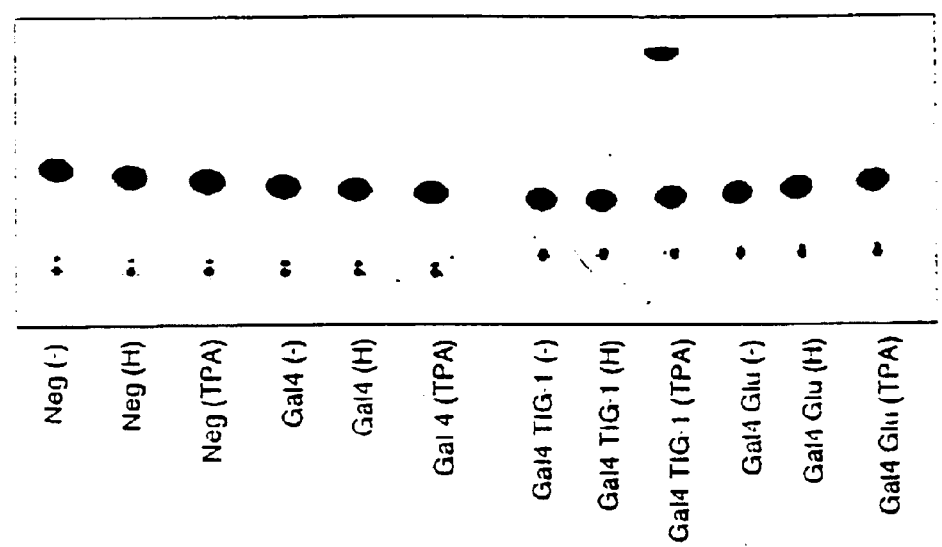
Figure 7:
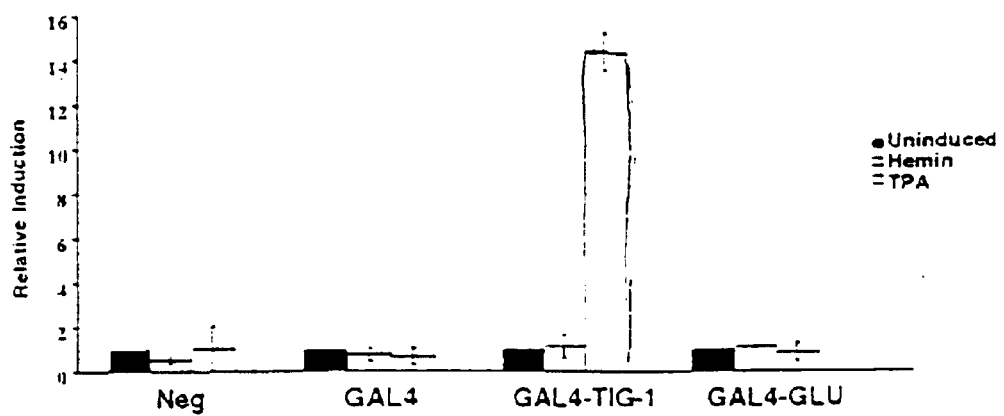

Strikingly, TPA induced K562 cells cotransfected with the CAT reporter construct and the GAL4-TIG-1 expression vector increased cat gene expression by 11–14 fold as compared to uninduced cells, after normalization for transfection efficiency and the non-specific effects of TPA, as shown in FIG. 7. panel C: GAL4-TIG-1 open bar. No such effect of TPA induction on K562 cells was found with any of the other plasmids cotransfected in this experiment (FIG. 7C except for GAL4-TIG-1). This result suggests that TPA induction of protein kinase C activity may result in regulation of the transcriptional activity of the TIG-1 protein. A putative protein kinase C phosphorylation site is found at amino acids 428–430 of the deduced open reading frame as depicted in FIG. 4.

The results of the cotransfection assays suggest that the TIG-1 protein could function as a transcriptional activating factor, when tethered to DNA. Since a specific DNA binding domain could not be deduced, it is hypothesized that the TIG-1 protein may function as a transcriptional coactivator factor especially following induction of protein kinase C activity. Glutamine rich proteins have been observed as coactivators of transcriptions such as TAF110 (Hoey et. al.). Indeed, there are two classes of glutamine rich transcriptional regulatory proteins; one class including proteins such as TAF110 and TIG-1 contain clusters of glutamine residues, the other class including such proteins as nuclear respiratory factors 1 and 2 and Sp1 have glutamine containing clusters of hydrophobic residues (Gugneja et. al. 1996, Gill et. al. 1994). Glutamine rich proteins can form stable oligomers with other glutamine rich proteins as the polyglutamine tracts form β-pleated sheets that can form polar zippers (Stott et. al. 1995, Perutz, 1996).

Tjian's group identified a co-activator complex (ARC) that mediates chromatin-directed transcriptional activation. Naar et. al. identified one of the members of the ARC complex as a polypeptide of approximate molecular weight 105 kDa. Microsequence analysis of this polypeptide yielded two peptide fragments that were identical to peptides corresponding to the deduced open reading frame of the TIG-1 mRNA. The two peptides fragments were identical to amino acids 13–22 and 501–512 of the deduced open reading frame of TIG-1 mRNA (Naar et. al. 1999).

Using the affinity purified rabbit antiserum to the carboxy terminal 185 amino acids of TIG-1 protein reported in this paper, Naar et. al. was able to immunoprecipitate the ARC complex and demonstrate that it was identical to the ARC complex that was purified using (affinity chromatography for) the transcriptional activation domain of VP-16.

Highly related, if not identical to the ARC complex, is the DRIP complex identified by Freedman's group (Rachez et. al. 1999). The DRIP complex helps to mediate ligand-dependent transcription by such nuclear activators as the vitamin D and thyroid hormone receptors. The ARC and DRIP complexes share many proteins in common; the DRIP complex prepared from HeLa cell nuclear extracts contains the TIG-1 protein (Naar et. al., 1999).

These transcriptional activator complexes appear to be found in all cells; furthermore there appears to be equal stoichiometry of the proteins within each complex. Though TIG-1 mRNA appears to be ubiquitously expressed, data demonstrates that at least at the level of mRNA expression there is substantial variation in the amount of TIG-1 mRNA with highest levels of expression in placenta and bone marrow derived tissues. If indeed there is concomitant variation in expression of TIG-1 protein, it is possible that TIG-1 protein may participate in multiple complexes or in particular tissues to function in a tissue specific manner.

Whether TIG-1 protein directly interacts with transcriptional activators or serves some other function within the transcriptional activator complex remains to be determined. Which members of ARC interact directly interact with TIG-1 protein may be answered by expression of the TIG-1 protein in a yeast two hybrid system.

Further studies to determine whether the activity of the TIG-1 protein is regulated by phosphorylation are warranted based on the transfection data. Whether the TIG-1 protein serves a unique function in the cell, or can be replaced by other members of the ARC complex will require gene knockout experiments.

It is of interest that the TIG-1 mRNA encoding for a protein found to be part of a chromatin altering complex was independently identified using a subtractive hybridization protocol aimed at identifying novel genes encoding for proteins involved in differentiation of the human leukemia cell line K562. Expression of TIG-1 mRNA was noted in hemin induced K562 cells, however, its expression was increased 2.5 fold when the K562 cells were induced with TPA. Since the phenotype of the K562 cell switches from erythroid to megakaryocytoid it is possible that the TIG-1 protein/ARC complex is required for remodeling of chromatin structure at megakaryocytic specific promoters and enhancement of gene expression by a tissue specific subset of transcription factors. Indeed, induction of K562 cells with hemin results in a very specific alteration of chromatin structure especially within and around the K562 cell β-globin gene domain-including alteration at the locus control region (LCR) leading to expression of epsilon and gamma globin genes (Tuan et. al., 1985); induction of K562 cells with TPA does not result in alteration of the chromatin structure of the β-globin LCR, extinguishes erythroid specific gene expression, while activating expression of other sets of genes-presumably requiring alteration of the chromatin structure, possibly by ARC/DRIP at the promoter/enhancers of these genes. Our data suggest that there is variation in the level of TIG-1 mRNA expression in tissues with highest levels of expression in the placenta and bone marrow derived tissues; whether TIG-1 protein participates complexes other than ARC/DRIP remains to be determined.

Transfection of the expression vector encoding for the GAL4:TIG-1 fusion protein into K562 cells did result in some change in K562 cell morphology. Whether the TIG-1 protein plays a role in the TPA induced megakaryocytoid differentiation of K562 cells remains to be determined.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

REFERENCES

Alitalo, R., et al., "Enhanced expression of transforming growth factor beta during megakaryoblast differentiation of K562 leukemia cell line," *BLOOD*, 71: 899–901 (1988);

Alitalo, R., et al. "Increased erythroid potentiating activity/tissue inhibitor of metalloproteinase and jun/fos transcription factor complex characterize tumor promoter induced megakaryocytic differentiation of K562 leukemia cells," *BLOOD*, 75: 1974–1982 (1990);

Andersson, L. C., et al. "Induction of erythroid differentiation in the human leukemia cell line K562," Nature, 278: 364–365 (1990);

Bayer, E. A., et al., Meth Enzym 62:308 (1979);

Campbell, A. M., *Monoclonal Antibody Technology: Laboratory Techniques in Biochemistry and Molecular Biology*, Elsevier Science Publishers, Amsterdam, The Netherlands (1984);

Capecchi, M., Cell 22:479–488 (1980);

Charnay, P. et al. "Transcriptional regulation of globin gene expression in the human erythroid cell line K562," *Science* 220: 1281–1283 (1983);

Cox, G. W., et al. "Molecular cloning and characterization of a novel macrophage gene that encodes a nuclear protein comprising polyglutamine repeats and interspersing histidines" *J. Biol. Chem.*, 271: 25515–25523 (1996);

Dean, A., et al. "Inducible transcription of five globin genes in K562 leukemia cells," *Proc Natl Acad Sci USA*, 80: 5515–5519 (1983);

Dignam, J., et al. "Accurate transcription initiation by RNA polymerase II in a soluble extract from isolated mammalian nuclei," *Nuc. Acid. Res.*, 11: 1475–1489 (1983);

Engval, E., et al., Immunol 109:129 (1972);

Goding, J. W., J Immunol Meth 13:215 (1976);

Gerber H. P., et al. "Transcriptional activation modulated by homopolymeric glutamine and proline stretches," *Science*, 263: 808–811 (1994);

Gill, et al., "A glutamine-rich hydrophobic patch in transcription factor Sp1 contacts the dTAF$_{II}$110 component of the Drosophila TFIID complex and mediates transcriptional activation," *Proc. Natl. Acad. Sci. USA*, 91: 192–196 (1994);

Gugneja, S., et al., "Nuclear respiratory factors 1 and 2 utilize similar Glutamine-containing clusters of hydrophobic residues to activate transcription," *Mol. Cell. Biol.*, 16: 5708–5716 (1996);

Hoey, T., et al., "Molecular cloning and functional analysis of Drosophila TAF110 reveal properties of coactivators," *Cell*, 72: 247–260 (1991);

Innis, et al., *PCR Protocols*, Academic Press, San Diego, Calif. (1990);

Klein, T. M., et al., Nature 327:70–73 (1987);

Lin, C-H., et al., "Phorbol ester induction of differentiation and apoptosis in the K562 cell line is accompanied by marked decreases in the stability of globin mRNAs and decreases in the steady state level of mRNAs encoding for ribosomal proteins L35, L31, L27 and L21," *Cellular and Molecular Biology Research*, 40: 13–26 (1994);

Lumelsky, N. et al., "Negative regulation of globin gene expression during megakaryocytic differentiation of a human erythroleukemia cell line," *Mol. Cell. Biol.*, 11: 3528–3536 (1991);

Lutz, et al., Exp Cell Res 175:109–124 (1988);

Mannino, R. J. and Gould-Fogerite, S., BioTechniques 6:682–690 (1988);

Miller, L. K., Bioessays 11:91–95 (1989);

Naar, A. M., et al., "Composite co-activator ARC mediates chromatin-directed transcriptional activation," *Nature*, 398: 828–83 (1999);

Needleman and Wunsch, J Mol Biol 48:443 (1970);

Pearson and Lipman, Proc Natl Acad Sci USA 85:2444 (1988);

Perutz, M. F., "Glutamine repeats and inherited neurodegenerative diseases: molecular aspects," *Current Opinion in Structural Biology*, 6: 848–858 (1996);

Rachez, R., et al., "Ligand-dependent transcription activation by nuclear receptors requires the DRIP complex," *Nature*, 398: 824–828 (1999);

Ross, L. M., et al., "cDNAs with long CAG trinucleotide repeats from human brain," *Human Genetics*, 100: 114–122 (1997);

Sambrook et al., *Molecular Cloning: A Laboratory Manual*, 2d Edition, Cold Spring Harbor Laboratory Press, Cold Spring Harbor, N.Y. (1989);

Shigekawa, K. and Dower, W. J., BioTechniques 6:742–751 (1988);

Siebert, P. D., et al., "Positive and Negative Regulation of Specific Gene Expression by the Tumor Promoter TPA in Human Erythroleukemic K562 Cells," *Prog. Clin. Bio. Res.*, 191: 233–248 (1985);

Smith and Waterman, Adv Appl Math 2:482 (1981);

Sternberger, L. A., et al., J Histochem Cytochem 18:315 (1970).

St. Groth, et al., J Immunol Methods 35:1–21 (1980).

Stott, K., et al., "Incorporation of Glutamine Repeats Makes Proteins Oligomerize: Implications For Neurodegenerative Diseases," *Proc. Natl. Acad. Sci. USA*, 92: 6509–6513 (1995);

Tuan D. et al., "β-like-gene Domain in Human Erythroid Cells," *Proc. Natl. Acad. Sci. USA*, 82: 6384–6388 (1985);

Wang, Z., et al., "A gene expression screen," *Proc. Natl. Acad. Sci. USA*, 88: 11505–11509 (1991).

What is claimed is:

1. An isolated nucleic acid molecule wherein said nucleic acid molecule encodes an amino acid sequence as shown in SEQ ID NO:3.

2. The isolated nucleic acid molecule of claim 1 wherein said nucleic acid molecule has a nucleotide sequence as shown in SEQ ID NO:1.

3. The isolated nucleic acid molecule of claim 1 wherein said nucleic acid is deoxyribonucleic acid.

4. The isolated nucleic acid molecule of claim 3 wherein said deoxyribonucleic acid is cDNA.

5. The isolated nucleic acid molecule of claim 1 wherein said nucleic acid is ribonucleic acid.

6. The isolated nucleic acid molecule of claim 5 wherein said ribonucleic acid is mRNA.

7. The isolated nucleic acid molecule of claim 1 wherein said nucleic acid encodes a transcriptional activity.

8. An expression vector comprising the nucleic acid molecule of claim 1.

9. The expression vector of claim 8 wherein said expression vector is selected from the group consisting of a plasmid and a virus.

10. A cell comprising the nucleic acid molecule of claim 1.

11. A cell comprising the expression vector of claim 8.

12. A method of decreasing expression of a having transcriptional activation activity in a host cell, said method comprising introducing the oligonucleotide fully complementary to the mRNA of claim 6 into the cell, wherein said oligonucleotide blocks translation of said mRNA so as to decrease expression of said transcriptional activator protein in said host cell.

13. A method of increasing expression of transcriptional activator protein in a host cell, said method comprising:

introducing the nucleic acid molecule of claim 1 into the cell; and allowing said cell to express said nucleic acid molecule resulting in the production of transcriptional activator protein in said cell.

14. A method of screening a substance for the ability of the substance to modify transcriptional activator protein function, said method comprising:

introducing the nucleic acid molecule of claim 1 into a host cell;

expressing said transcriptional activator protein encoded by said nucleic acid molecule in the host cell;

exposing the cell to a substance; and evaluating the exposed cell to determine if the substance modifies the function of the transcriptional activator protein.

15. The method of claim 14 wherein said evaluation comprises monitoring the expression of transcriptional activator protein.

16. A method of obtaining DNA encoding a transcriptional activator protein, said method comprising:

selecting a DNA molecule encoding a transcriptional activator protein, said DNA molecule having a nucleotide sequence as shown in SEQ ID NO:1;

designing an oligonucleotide probe for a transcriptional activator protein based on the nucleotide sequence of the selected DNA molecule;

probing a genomic or cDNA library of an organism with the oligonucleotide probe; and obtaining clones from said library that are recognized by said oligonucleotide probe, so as to obtain DNA encoding a transcriptional activator protein.

17. A method of obtaining DNA encoding a transcriptional activator protein, said method comprising:

selecting a DNA molecule encoding a transcriptional activator protein, said DNA molecule having a nucleotide sequence as shown in SEQ ID NO:1;

designing degenerate oligonucleotide primers based on the nucleotide sequence of the selected DNA molecule; and utilizing said oligonucleotide primers in a polymerase chain reaction on a DNA sample to identify homologous DNA encoding a transcriptional activator protein in said sample.

* * * * *